United States Patent
Hoarau

(10) Patent No.: US 8,690,864 B2
(45) Date of Patent: Apr. 8, 2014

(54) SYSTEM AND METHOD FOR CONTROLLING TISSUE TREATMENT

(75) Inventor: Carine Hoarau, Lafayette, CA (US)

(73) Assignee: Covidien LP, Mansfield, MA (US)

( * ) Notice: Subject to any disclaimer, the term of this patent is extended or adjusted under 35 U.S.C. 154(b) by 1694 days.

(21) Appl. No.: 11/716,260

(22) Filed: Mar. 9, 2007

(65) Prior Publication Data

US 2008/0221409 A1    Sep. 11, 2008

(51) Int. Cl.
*A61B 18/18*    (2006.01)

(52) U.S. Cl.
USPC ............................... 606/21; 606/20

(58) Field of Classification Search
USPC .......................... 606/41–42, 20–26
See application file for complete search history.

(56) References Cited

U.S. PATENT DOCUMENTS

| | | | |
|---|---|---|---|
| 3,998,550 A | 12/1976 | Konishi et al. | |
| 4,066,068 A | 1/1978 | Nilsson et al. | |
| 4,364,008 A | 12/1982 | Jacques | |
| 4,711,244 A | 12/1987 | Kuzara | |
| 4,723,554 A | 2/1988 | Oman et al. | |
| 4,732,149 A * | 3/1988 | Sutter | 606/51 |
| 4,805,623 A | 2/1989 | Jobsis | |
| 4,850,365 A | 7/1989 | Rosenthal | |
| 4,860,753 A | 8/1989 | Amerena | |
| 4,883,055 A | 11/1989 | Merrick | |
| 4,907,594 A | 3/1990 | Muz | |
| 4,911,167 A | 3/1990 | Corenman et al. | |
| 5,057,695 A | 10/1991 | Hirao et al. | |
| 5,086,781 A | 2/1992 | Bookspan | |
| 5,111,817 A | 5/1992 | Clark et al. | |
| 5,146,091 A | 9/1992 | Knudson | |
| 5,217,460 A * | 6/1993 | Knoepfler | 606/52 |
| 5,224,478 A | 7/1993 | Sakai et al. | |
| 5,277,181 A | 1/1994 | Mendelson et al. | |
| 5,279,295 A | 1/1994 | Martens et al. | |
| 5,282,467 A | 2/1994 | Piantadosi et al. | |

(Continued)

FOREIGN PATENT DOCUMENTS

| | | |
|---|---|---|
| CA | 2353007 A1 | 6/2000 |
| DE | 19855521 A1 | 6/2000 |

(Continued)

OTHER PUBLICATIONS

International Search Report PCT/US2008/0003030, 4 pages, mailed Sep. 3, 2008.

(Continued)

*Primary Examiner* — Linda Dvorak
*Assistant Examiner* — Jaymi Della
(74) *Attorney, Agent, or Firm* — Fletcher Yoder

(57) ABSTRACT

Embodiments of the present invention relate to a system and method for controlling a tissue treatment device using results from a spectroscopic tissue analyzer. One embodiment provides a system that uses a direct signal from a spectroscopic tissue analyzer to control the tissue treatment device. Alternatively, the system may provide an audible feedback signal to a user, allowing the user to choose how to adjust the tissue treatment device. A final embodiment provides a probe that has active sites for treating tissue, and an optical system to convey light to the active sites, allowing an analysis of the tissue parameter at the active sites.

12 Claims, 6 Drawing Sheets

(56) References Cited

U.S. PATENT DOCUMENTS

| | | |
|---|---|---|
| 5,337,745 A | 8/1994 | Benaron |
| 5,337,937 A | 8/1994 | Remiszewski et al. |
| 5,348,004 A | 9/1994 | Hollub |
| 5,355,880 A | 10/1994 | Thomas et al. |
| 5,377,674 A | 1/1995 | Kuestner |
| 5,433,717 A * | 7/1995 | Rubinsky et al. ............... 606/20 |
| 5,499,627 A | 3/1996 | Steuer et al. |
| 5,615,689 A | 4/1997 | Kotler |
| 5,645,059 A | 7/1997 | Fein et al. |
| 5,687,721 A | 11/1997 | Kuhls |
| 5,701,902 A | 12/1997 | Vari et al. |
| 5,720,284 A | 2/1998 | Aoyagi et al. |
| 5,735,284 A | 4/1998 | Tsoglin et al. |
| 5,747,789 A | 5/1998 | Godik |
| 5,755,672 A | 5/1998 | Arai et al. |
| 5,762,609 A * | 6/1998 | Benaron et al. ............... 600/473 |
| 5,788,643 A | 8/1998 | Feldman |
| 5,803,908 A | 9/1998 | Steuer et al. |
| 5,827,181 A | 10/1998 | Dias et al. |
| 5,833,602 A | 11/1998 | Osemwota |
| 5,853,364 A | 12/1998 | Baker, Jr. et al. |
| 5,860,919 A | 1/1999 | Kiani-Azarbayjany et al. |
| 5,906,582 A | 5/1999 | Kondo et al. |
| 6,064,898 A | 5/2000 | Aldrich |
| 6,125,297 A | 9/2000 | Siconolfi |
| 6,149,591 A | 11/2000 | Borgos et al. |
| 6,178,342 B1 | 1/2001 | Thompson et al. |
| 6,222,189 B1 | 4/2001 | Misner et al. |
| 6,246,894 B1 | 6/2001 | Steuer et al. |
| 6,280,396 B1 | 8/2001 | Clark et al. |
| 6,336,044 B1 | 1/2002 | Ghiassi et al. |
| 6,370,426 B1 | 4/2002 | Campbell et al. |
| 6,400,971 B1 | 6/2002 | Finarov et al. |
| 6,402,690 B1 | 6/2002 | Rhee et al. |
| 6,442,408 B1 | 8/2002 | Wenzel et al. |
| 6,466,807 B1 | 10/2002 | Dobson et al. |
| 6,488,677 B1 | 12/2002 | Bowman et al. |
| 6,512,936 B1 | 1/2003 | Monfre et al. |
| 6,591,122 B2 | 7/2003 | Schmitt |
| 6,592,574 B1 | 7/2003 | Shimmick et al. |
| 6,600,946 B1 | 7/2003 | Rice |
| 6,606,509 B2 | 8/2003 | Schmitt |
| 6,615,064 B1 | 9/2003 | Aldrich |
| 6,635,491 B1 | 10/2003 | Khalil et al. |
| 6,636,759 B2 | 10/2003 | Robinson |
| 6,643,543 B2 | 11/2003 | Takehara et al. |
| 6,654,620 B2 | 11/2003 | Wu et al. |
| 6,668,181 B2 | 12/2003 | Wenzel et al. |
| 6,675,029 B2 | 1/2004 | Monfre et al. |
| 6,687,519 B2 | 2/2004 | Steuer et al. |
| 6,777,240 B2 | 8/2004 | Hazen et al. |
| 6,849,046 B1 | 2/2005 | Eyal-Bickels |
| 6,873,865 B2 | 3/2005 | Steuer et al. |
| 6,882,874 B2 | 4/2005 | Huiku |
| 6,950,699 B1 | 9/2005 | Manwaring et al. |
| 6,961,598 B2 | 11/2005 | Diab |
| 7,027,849 B2 | 4/2006 | Al-Ali |
| 7,142,901 B2 | 11/2006 | Kiani et al. |
| 7,215,991 B2 | 5/2007 | Besson et al. |
| 7,236,811 B2 | 6/2007 | Schmitt |
| 7,239,902 B2 | 7/2007 | Schmitt et al. |
| 7,277,741 B2 | 10/2007 | Debreczeny et al. |
| 7,283,242 B2 | 10/2007 | Thornton |
| 7,343,186 B2 | 3/2008 | Lamego et al. |
| 7,430,444 B2 | 9/2008 | Pologe et al. |
| 7,657,292 B2 | 2/2010 | Baker et al. |
| 8,135,448 B2 | 3/2012 | Baker et al. |
| 8,180,419 B2 | 5/2012 | Debreczeny et al. |
| 2001/0020122 A1 | 9/2001 | Steuer et al. |
| 2002/0026188 A1 * | 2/2002 | Balbierz et al. ............... 606/41 |
| 2003/0060693 A1 | 3/2003 | Monfre et al. |
| 2003/0220548 A1 | 11/2003 | Schmitt |
| 2004/0127777 A1 | 7/2004 | Richti et al. |
| 2004/0147034 A1 | 7/2004 | Gore et al. |
| 2004/0230106 A1 | 11/2004 | Schmitt et al. |
| 2005/0070773 A1 | 3/2005 | Chin et al. |
| 2005/0119538 A1 | 6/2005 | Jeon et al. |
| 2005/0131286 A1 | 6/2005 | Parker et al. |
| 2005/0168722 A1 | 8/2005 | Forstner et al. |
| 2005/0192488 A1 | 9/2005 | Bryenton et al. |
| 2005/0192493 A1 | 9/2005 | Wuori |
| 2005/0203357 A1 | 9/2005 | Debreczeny et al. |
| 2005/0250998 A1 | 11/2005 | Huiku |
| 2005/0251124 A1 * | 11/2005 | Zvuloni et al. ............... 606/21 |
| 2005/0267346 A1 | 12/2005 | Faber et al. |
| 2006/0020181 A1 | 1/2006 | Schmitt |
| 2006/0025760 A1 | 2/2006 | Podhajsky |
| 2006/0052680 A1 | 3/2006 | Diab |
| 2006/0084864 A1 | 4/2006 | Schmitt et al. |
| 2006/0122475 A1 | 6/2006 | Balberg et al. |
| 2006/0129037 A1 | 6/2006 | Kaufman et al. |
| 2006/0129038 A1 | 6/2006 | Zelenchuk et al. |
| 2006/0167350 A1 | 7/2006 | Monfre et al. |
| 2006/0247506 A1 | 11/2006 | Balberg et al. |
| 2006/0253016 A1 | 11/2006 | Baker, Jr. et al. |
| 2006/0276696 A1 | 12/2006 | Schurman |
| 2007/0032707 A1 | 2/2007 | Coakley et al. |
| 2007/0032709 A1 | 2/2007 | Coakley et al. |
| 2007/0032710 A1 | 2/2007 | Raridan et al. |
| 2007/0032711 A1 | 2/2007 | Coakley et al. |
| 2007/0032712 A1 | 2/2007 | Raridan et al. |
| 2007/0032713 A1 | 2/2007 | Eghbal et al. |
| 2007/0073122 A1 | 3/2007 | Hoarau |
| 2007/0073123 A1 | 3/2007 | Raridan, Jr. |
| 2007/0073125 A1 | 3/2007 | Hoarau et al. |
| 2007/0073126 A1 | 3/2007 | Raridan, Jr. |
| 2007/0073127 A1 | 3/2007 | Kiani et al. |
| 2007/0073128 A1 | 3/2007 | Hoarau et al. |
| 2007/0078309 A1 | 4/2007 | Matlock |
| 2007/0078311 A1 | 4/2007 | Al-Ali et al. |
| 2007/0106137 A1 | 5/2007 | Baker, Jr. et al. |
| 2007/0118027 A1 | 5/2007 | Baker, Jr. et al. |
| 2007/0129614 A1 | 6/2007 | Schmitt et al. |
| 2007/0167693 A1 | 7/2007 | Scholler et al. |
| 2007/0244376 A1 | 10/2007 | Wang |
| 2007/0260129 A1 | 11/2007 | Chin |
| 2007/0260130 A1 | 11/2007 | Chin |
| 2007/0260131 A1 | 11/2007 | Chin |
| 2007/0282178 A1 | 12/2007 | Scholler et al. |
| 2007/0282183 A1 | 12/2007 | Scholler et al. |
| 2008/0004513 A1 | 1/2008 | Walker et al. |
| 2008/058622 A1 | 3/2008 | Baker |
| 2008/0076980 A1 | 3/2008 | Hoarau |
| 2008/0076981 A1 | 3/2008 | Hoarau |
| 2008/0076994 A1 | 3/2008 | Hoarau |
| 2008/0076995 A1 | 3/2008 | Hoarau |
| 2008/0076996 A1 | 3/2008 | Hoarau |
| 2008/0081969 A1 | 4/2008 | Feldman et al. |
| 2008/0097173 A1 | 4/2008 | Soyemi et al. |
| 2008/0154104 A1 | 6/2008 | Lamego et al. |

FOREIGN PATENT DOCUMENTS

| | | |
|---|---|---|
| EP | 1135184 A1 | 6/2000 |
| EP | 1184663 A2 | 3/2002 |
| EP | 1491135 | 12/2004 |
| FR | 2710517 | 4/1995 |
| JP | 04-040940 | 2/1992 |
| JP | 5-329163 | 12/1993 |
| JP | 11-244266 | 9/1999 |
| JP | 2004 081427 A | 3/2004 |
| JP | 25169020 | 6/2005 |
| JP | 25278758 | 10/2005 |
| JP | 26075354 | 3/2006 |
| WO | WO 93/13706 A2 | 7/1993 |
| WO | WO 95/19562 A | 7/1995 |
| WO | WO 98/27865 A | 7/1998 |
| WO | WO 98/34097 | 8/1998 |
| WO | WO 00/32262 A1 | 6/2000 |
| WO | WO 00/71025 A1 | 11/2000 |
| WO | WO 01/16577 A1 | 3/2001 |
| WO | WO 01/74252 A | 10/2001 |

(56) References Cited

FOREIGN PATENT DOCUMENTS

| WO | WO 03/010510 A | 2/2003 |
|---|---|---|
| WO | WO 2005/041765 A | 5/2005 |
| WO | WO2006124455 | 11/2006 |

OTHER PUBLICATIONS

U.S. Appl. No. 11/528,154, filed Sep. 27, 2006, Debreczeny et al.
U.S. Appl. No. 11/528,218, filed Sep. 27, 2006, Campbell, et al.
U.S. Appl. No. 11/529,024, filed Sep. 28, 2006, Agashe, et al.
U.S. Appl. No. 11/541,010, filed Sep. 29, 2006, Baker, Jr., et al.
Wheeler, Owen H., "Near Infrared Spectra of Organic Compounds," Department of Chemistry, College of Agriculture and Mechanic Arts, University of Puerto Rico (Mar. 1929).
Pace, Nello, et al., "Studies on Body Composition: III. The body water and chemically combined nitrogen content in relation to fat content," Naval Medical Research Institute, Bethesda, Maryland (Jan. 11, 1945).
Mitchell, H. M., et al., The Chemical Composition of the Adult Human Body and Its bearing on the Biochemistry of Growth), Division of Animal Nutrition, Departments of Physiology and Animal Husbandry, University of Illinois, pp. 625-637 (Feb. 1945).
Schloerb, Paul R., et al., "The Measurement of Total Body Water in the Human Subject by Deuterium Oxide Dilution," *Surgical Research Laboratories of the Peter Bent Brigham Hospital, and the Department of Surgery and the Biophysical Laboratory of the Harvard Medical School*, pp. 1296-1310 (Mar. 20, 1950).
Forbes, R.M., et al., "The Composition of the Adult Human Body as Determined by Chemical Analysis," Division of Animal Nutrition, and the Department of Anatomy, University of Illinois, Jan. 19, 1953.
Buijs, K., et al., "Near-Infrared Studies of the Structure of Water. I. Pure Water," *The Journal of Chemical Physics*, vol. 39, No. 8, pp. 2035-2041 (Oct. 15, 1963).
Choppin, G.R., et al., "Near-Infrared Studies of the Structure of Water. II. Ionic Soluation," *The Journal of Chemical Physics*, vol. 39, No. 8, pp. 2042-2050 (Oct. 15, 1963).
Goldstein, R., et al., "The Near-Infrared Absorption of Liquid Water at Temperatures Between 27 and 209° C.," *J. Quant. Spectrosc. Radiat. Transfer.*, vol. 4, pp. 441-451 (1964).
Ben-Gera, I., et al., "Influence of Fat Concentration on the Absorption Spectrum of Milk in the Near-Infrared Region," *Israel J. Agric. Res.*, Vo. 18, No. 3, pp. 117-124 (Jul. 1968).
Houseman, R.A., et al., "The measurement of total body water in living pigs by deuterium oxide dilution and its relation to body composition," *Br. J. Nutr.*, vol. 30, pp. 149-156 (1973).
Krikorian, S. Edward, et al., "The identification and origin of N-H overtone and combination bands in the near-infrared spectra of simple primary and secondary amides," *Spectrochimica Acta*, vol. 29A, pp. 1233-1246 (1973).
Lesser, G.T., et al., "Body water compartments with human aging using fat-free mass as the reference standard," *Am J. Physiol Regul Integr Comp Physiol.*, vol. 236, pp. 215-220 (1979).
Sheng, Hwai-Ping, et al., "A review of body composition studies with emphasis on total body water and fat," *The American Journal of Clinical Nutrition*, vol. 32., pp. 630-647 (Mar. 1979).
Martens, H., et al., "Unscrambling Multivariate Data from Mixtures: I: Fat, water and protein determination in meat by near-infrared reflectance spectroscopy, II: soy protein and collagen determination in meat products from amino acid data," *Meat Res. Workers, Proc. European Meeting*, pp. 146-149 (1980).
Fomon, Samuel J., et al., "Body composition of reference children from birth to age 10 years," The American Journal of clinical Nutrition, vol. 35, pp. 1169-1175, (May 1982).
Lanza, Elaine, "Determination of Moisture, Protein, Fat, and Calories in Raw Pork and Beef by near Infrared Spectroscopy," *Journal of Food Science*, vol. 48, pp. 471-474 (1983).
Shields, R. G., Jr., et al., "Efficacy of Deuterium Oxide to Estimate Body Composition of Growing Swine"; *Journal of Animal Science*, vol. 57, No. 1, pp. 66-73, (1983).

Wolfgang, Arneth, "Multivariate Infrared and near-infrared Spectroscopy: rapid analysis of protein, fat and water in meat," *Food Res and Data Analysis, Proc from IUoST Symp*, Oslo, Norway, pp. 239-251 (1983).
Cohn, S.H., et al., "Assessment of cellular mass and lean body mass by noninvasive nuclear techniques," *J. Lab Clin Med.*, vol. 105, pp. 305-311 (1985).
Hannon, John P., et al., "Splenic red cell sequestration and blood volume measurements in conscious pigs," *Am J. Physiol.*, vol. 248, pp. R293-R301 (1985).
Potts, R.O., et al., "A Noninvasive, In Vivo Technique to Quantitatively measure Water Concentration of the Stratum Corneum Using Attenuated Total-Reflectance Infrared Spectroscopy," *Arch. Dermatol Res.*, vol. 277, pp. 489-495 (1985).
Cox, Patrick, et al., "Variations in Lipids in Different Layers of Porcine Epidermis," *J. Invest Dermatol.*, vol. 87, pp. 741-744 (1986).
Valdes, E. V., et al., "Determination of Crude Protein and Fat in Carcass and Breast Muscle Samples of Poultry by Near Infrared Reflectance Spectroscopy," *Poultry Science*, vol. 65, pp. 485-490 (1986).
Hedberg, Chrisopher L., et al., "The Time Course of Lipid Biosynthesis in Pig Epidermis," *J. Invest Dermatol.*, vol. 91, pp. 169-174 (1988).
Hedberg, Christopher L., et al., "The nonpolar Lipids of Pig Epidermis," *J. Invest Dermatol.*, vol. 90, pp. 225-229 (1988).
Trapp, Scott A., et al., "An improved spectrophotometric bromide assay for the estimation of extracellular water volume," *Clinica Chimica Acta.*, vol. 181, pp. 207-212, (1989).
Bommannan, D., et al., "Examination of Stratum Corneum Barrier Function In Vivo by Infrared Spectroscopy," *J. Invest Dermatol*, vol. 95, pp. 403-408 (1990).
Hannon, John P., et al., "Normal pHysiological Values for Conscious Pigs Used in Biomedical Research," *Laboratory Animal Science*, vol. 40, No. 3, May 1990.
Mak, Vivien H.W., et al., "Oleic Acid Concentration and Effect in Human Stratum Corneum: Non-Invasive determination by Attenuated Total Reflectance Infrared Spectroscopy In Vivo," *Journal of Controlled Release*, vol. 12, pp. 67-75 (1990).
Edwardson, P. et al., "The Use of FT-IR for the Determination of Stratum Corneum Hydration in Vitro and in Vivo," J. *of Pharmaceutical & Biomed. Analysis*, vol. 9, Nos. 10-12, pp. 1089-1094, 1991.
Drummer, C., et al., "Effects of an acute saline infusion on fluid and electrolyte metabolism in humans," *Am J. Physiol.*, vol. 262, pp. F744-F754 (1992).
Horber, F.F., et al., "Impact of hydration status on body composition as measured by dual energy X-ray absorptiometry in normal volunteers and patients on haemodialysis," *The British Journal of Radiology*, vol. 65, pp. 895-900 (1992).
Schmitt et al., *Proc. SPIE*, "Measurement of blood hematocrit by dual-wavelength near-IP photoplethysmography," 1641:150-161 (1992).
Diaz-Carrillo, E., et al., "Near infrared calibrations for goat's milk components; protein, total casein, $\alpha_s$-, $\beta$- and $\kappa$-caseins, fat and lactose," *J. near Infrared Spectrosc.*, vol. 1, pp. 141-146 (1993).
Martin, K., "Direct Measurement of Moisture in Skin by NIR spectroscopy," *J. Soc. Cosmet. Chem.*, 44:249-261 (1993).
Richard, Stéphanie, et al., "Characterization of the Skin In Vivo by High Resolution Magnetic Resonance Imaging: Water Behavior and Age-Related Effects," *The Journal of Investigative Dermatology*, vol. 100, No. 5, pp. 705-709 (May 1993).
Thompson et al., "Can bioelectrical impedance be used to measure total body water in dialysis patients?", *Physiol. Meas.*, 14:455-461 (1993).
Bewig, Karen M., et al., "Discriminant Analysis of Vegetable Oils by Near-Infrared Reflectance Spectroscopy," *JAOCS*, vol. 71, No. 2, pp. 195-200 (Feb. 1994).
Kamishikiryo-Yamashita, Hiromi, et al, "Protein Content in Milk by Near-Infrared Spectroscopy," *Journal of Food Science*, vol. 59, No. 2, pp. 313-315 (1994).
Matcher, S. J., et al., "Absolute quantification of deoxyhaemoglobin concentration in tissue near infrared spectroscopy," *Phys. Med. Biol.*, vol. 39, pp. 1295-1312 (1994).

(56) References Cited

OTHER PUBLICATIONS

Simanonok, Karl E., et al., "A Comprehensive Guyton Model Analysis of Physiologic Responses to Preadapting the Blood Volume as a Countermeasure to Fluid Shifts," *J. Clin Pharmacol*, vol. 34, pp. 440-453 (1994).

Steven, Alasdair C., et al., "Protein composition of cornified cell envelopes of epidermal keratinocytes," *Journal of Cell Science*, vol. 107, pp. 693-700 (1994).

Takeo, T. et al., "Skin Hydration State Estimation Using a Fiber-Optic Refractometer," *Applied Optics*, vol. 33, No. 19, Jul. 1994, p. 4267-72.

Warren, Joan L., et al., "The burden and Outcomes Associates with Dehydration among US Elderly, 1991," *American Journal of Public Health*, vol. 84, No. 8, pp. 1265-1269 (Aug. 1994).

Åneman, Anders, et al., "Splanchnic and Renal Sympathetic Activity in Relation to Hemodynamics During Isoflurane Administration in Pigs," *Anesth Analg.*, vol. 80, pp. 135-142, (1995).

Kisch, Hille, et al., "Accuracy and reproducibility of the measurement of actively circulating blood volume with an integrated fiberoptic monitoring system," *Critical Care Medicine*, vol. 23, No. 5, pp. 885-893 (1995).

Isaksson, Tomas, et al., "Non-Destructive Determination of Fat, Moisture and Protein in Salmon Fillets by Use of Near-Infrared Diffuse Spectroscopy," *J. Sci Food Agric.*, vol. 69, pp. 95-100 (1995).

Quiniou, N., et al., "Prediction of Tissular Body Composition from Protein and Lipid Deposition in Growing Pigs," *J. Anim. Sci.*, vol. 73, pp. 1567-1575, (1995).

Avis, N.J., et al.; "In vitro multifrequency electrical impedance measurements and modeling of the cervix in late pregnancy", *Physiological Measurement*, vol. 17, pp. A97-A103, 1996.

Gniadecka, M., et al., "Assessment of dermal water by high-frequency ultrasound: comparative studies with nuclear magnetic resonance," *British Journal of Dermatology*, vol. 135, pp. 218-224, (1996).

Finn, Patrick J., et al., "Progressive celluarl dehydration and proteolysis in critically ill patients," The Lancet, vol. 347, pp. 654-646 (Mar. 9, 1996).

Johnson et al., "Monitoring of Extracellular and Total Body Water during Hemodialysis Using Multifrequency Bio-Electrical Impedance Analysis," *Kidney and Blood Pressure Research*, 19:94-99 (1996).

Kotler, D.P., et al.; "Prediction of body cell mass, fat-free mass, and total body water with bioelectrical impedance analysis: effects of race, sex, and disease;" *Am J. Clin. Nutr*. 64(suppl):489S-97S (1996).

Kumar, Gitesh, et al., "Non-Invasive Optical Assessment of Tissue Hydration," *International conference on Biomedical Engineering*, Jun. 3-5, 1996, Hong Kong, pp. C2-C5.

Schmitt et al., *Proc. SPIE*, "Optimum wavelengths for measurement of blood hemoglobin content and tissue hydration by NIR spectrophotometry," 2678:442-453 (1996).

De Fijter, W.M., et al., "Assessment of total body water ad lean body mass from anthropometry, Watson formula, creatinine kinetics, and body electrical impedance compared with antipyrine kinetics and peritoneal dialysis patients," *Nephrol Dial Transplant*, vol. 12, pp. 151-156 (1997).

Johansen, Lars Bo, et al., "Hemodilution, central blood volume, and renal responses after an isotonic saline infusion in humans," *Am J. Physiol.*, vol. 272, pp. R549-R556 (1997).

Visser, Marjolein, et al., "Density of fat-free body mass: relationship with race, age, and level of body fatness," *Am J. Physiol.*, vol. 272, pp. E781-E787, (1997).

Alanen, Esko, et al., "Measurement of dielectric properties of subcutaneous fat with open-ended coaxial sensors," *Phys. Med. Biol.*, vol. 43, pp. 475-485 (1998).

Alanen, Esko, et al., "Variational Formulation of Open-Ended Coaxial line in Contact with Layered Biological Medium," *IEEE Transactions on Biomedical Engineering*, vol. 45, No. 10, pp. 1241-1248 (Oct. 1998).

Bonadonna, Riccardo C., et al., "Role of Tissue-Specific Blood Flow and Tissue Recruitment in Insulin-Mediated Glucose Uptake of Human Skeletal Muscl," *Circulation*, vol. 98, pp. 234-241, (1998).

Bracco, David, et al., "Bedside determination of fluid accumulation after cardiac surgery using segmental bioelectrical impedance," *Crit Care Med*, vol. 26, No. 6, pp. 1065-1070 (1998).

Gniadecka, Monika, et al., "Water and Protein Structure in Photoaged and Chronically Aged Skin," *J. Invest Dermatol*, vol. 111, pp. 1129-1133 (1998).

Gniadecka, Monika, et al., "Structure of Water, Proteins, and Lipids in Intact Human Skin, Hair, and Nail," *J. Invest Dermatol*, vol. 110, pp. 393-398 (1998).

Gow, Kenneth W., et al., "Effect of crystalloid administration on oxygen extraction in endotoxemic pigs," *J. Appl. Physiol.*, vol. 85, No. 5, pp. 1667-1675 (1998).

Husby, P., et al., "Midazolam-fentanyl-isoflurane anaesthesia is suitable for haemodynamic and fluid balance studies in pigs," *Laboratory Animals*, vol. 32, pp. 316-323 (1998).

Mitchell, A. D., et al., "Composition Analysis of Pork Carcasses by Dual-Energy X-Ray Absorptiometry," *J. Anim. Sci.*, vol. 76, pp. 2104-2114 (1998).

Mahan, D. C., et al., "Essential and Nonessential Amino Acid Composition of Pigs from Birth to 145 Kilograms of Body Weight, and Comparison to Other Studies," *J. Anim. Sci.*, vol. 76, pp. 513-521, (1998).

Martin, Kathleen, "In Vivo Measurements of Water in Skin by Near-Infrared Reflectance," *Applied Spectroscopy*, vol. 52, No. 7, 1998, pp. 1001-1007.

Schou, Henning, et al., "Uncompensated Blood Los is not Tolerated During Acute Normovolemic Hemodilution in Anesthetized Pigs," *Anesth Analg.*, vol. 87, pp. 786-794 (1998).

Stranc, M.F., et al., "Assessment of tissue viability using near-infrared spectroscopy," *British Journal of Plastic Surgery*, vol. 51, pp. 210-217, (1998).

Thomas, B. J., et al., "Bioimpedance Spectrometry in the Determination of Body Water Compartments: Accuracy and Clinical Significance," *Appl. Radiat. Isot.*, vol. 49, No. 5/6, pp. 447-455, (1998).

Wilhelm, K.P., "Possible Pitfalls in Hydration Measurements," *Skin Bioengineering Techniques and Applications in Dermatology and Cosmetology*, vol. 26, pp. 223-234 (1998).

Vrhovski, Bernadette, et al., "Biochemistry of tropoelastin," *Eur. J. Biochem.*, vol. 258, pp. 1-18 (1998).

Alanen, Esko, et al., "Penetration of electromagnetic fields of an open-ended coaxial probe between 1 MHz and 1 GHz in dielectric skin measurements," *Phys. Med. Biol.*, vol. 44, pp. N169-N176 (1999).

Dickens, Brian, et al., "Estimation of Concentration and Bonding Environment of Water Dissolved in Common Solvents Using Near Infrared Absorptivity," *J. Res. Natl. Inst. Stand. Technol.*, vol. 104, No. 2, pp. 173-183 (Mar.-Apr. 1999).

Fornetti, Willa C., et al., "Reliability and validity of body composition measures in female athletes," Journal of Applied Physiology, vol. 87, pp. 1114-1122, (1999).

Fusch, Christoph, et al., "Neonatal Body COmposition: Dual-Energy X-Ray Absorptiometry, Magnetic Resonance Imaging, and Three-Dimensional Chemical Shift Imaging versus Chemical Analysis in Piglets," *Pediatric Research*, vol. 46, No. 4, pp. 465-473 (1999).

Gudivaka, R., et al., "Single- and multifrequency models for bioelectrical impedance analysis of body water compartments," *J. Appl. Physiol.*, vol. 87, No. 3, pp. 1087-1096 (1999).

Jennings, Graham, et al., "The Use of infrared Spectrophotometry for Measuring Body Water Spaces," vol. 45, No. 7, pp. 1077-1081 (1999).

Kalantar-Zadeh, Kamyar, et al., "Near infra-red interactance for nutritional assessment of dialysis patients," *Nephrol Dial Transplant*, vol. 14, pp. 169-175 (1999).

Kayser-Jones, Jeanie, et al., "Factors Contributing to Dehydration in Nursing Homes: Inadequate Staffing and Lack of Professional Supervision," *J. Am Geriatr. Soc.*, vol. 47, pp. 1187-1194 (1999).

Lange, Neale R., et al., "The measurement of lung water," *Critical Care*, vol. 3, pp. R19-R24 (1999).

(56) References Cited

OTHER PUBLICATIONS

Marken Lichtenbelt, Wouter D. Van, et al., "Increased extracellular water compartment, relative to intracellular water compartment, after weight reduction," *Journal of Applied Physiology*, vol. 87, pp. 294-298 (1999).
Rennie, Michael J., "Perspectives—Teasing out the truth about collagen," *Journal of Physiology*, vol. 521, p. 1 (1999).
Sowa et al., "Near-infrared spectroscopic assessment of tissue hydration following surgery", *Journal of Surgical Research*, 86:62-69 (1999).
Wagner, J.R., et al., "Analysis of Body Composition Changes of Swine During Growth and Development," *J. Anim. Sci.*, vol. 77, pp. 1442-1466 (1999).
Wang, Zimian, et al., "Hydration of fat-free body mass: new physiological modeling approach," *Am. J. Physiol.*, vol. 276, pp. E995-E1003 (1999).
Wang, Zimian, et al., "Hydration of fat-free body mass: review and critique of a classic body-composition constant," *Am J. Clin. Nutr.*, vol. 69, pp. 833-841 (1999).
Ward, L., et al., "Multiple frequency bioelectrical impedance analysis: a cross-validation study of the inductor circuit and Cole models," *Physiol. Meas.*, vol. 20, pp. 333-347 (1999).
Wells, Jonathan CK, et al., "Four-component model of body composition in children: density and hydration of fat-free mass and comparison with simpler models," *Am J. Clin. Nutr.*, vol. 69, pp. 904-912 (1999).
Butte, Nancy F., et al., "Body Composition during the First 2 Years of Life; An Updated Reference," *Pediatric Research*, vol. 47, No. 5, pp. 578-585 (2000).
Feigenbaum, Matthew S., et al., "Contracted Plasma and Blood Volume in Chronic Heart Failure," *J Am Coll. Cardiol.*, vol. 35, No. 1, pp. 51-55 (Jan. 2000).
Kays, Sandra E., et al., "Predicting protein content by near infrared reflectance spectroscopy in diverse cereal food products," *J. Near Infrared Spectrosc.*, vol. 8, pp. 35-43 (2000).
Lucassen, G., et al., "Water Content and Water Profiles in Skin Measured by FTIR and Raman Spectroscopy," *Proc. SPIE*, vol. 4162, pp. 39-45 (2000).
Plank, L. D., et al., "Similarity of Changes in Body Composition in Intensive Care Patients following Severe Sepsis or Major Blunt Injury," *Annals New York Academy of Sciences*, pp. 592-602 (2000).
Ritz, P., et al., "Body Water Spaces and Cellular Hydration during Healthy Aging," *Annals New York Academy of Sciences*, pp. 474-483 (2000).
Schoeller, Dale, "Bioelectrical Impedance Analysis—What does it measure?" *Annals New York Academy of Sciences*, pp. 159-162 (2000).
Starcher, Barry C., "Lung Elastin and Matrix," *Chest*, vol. 117, No. 5, pp. 229S-234S, May 2000 Supplement.
Young, A.E.R., et al., "Behaviour of near-infrared light in the adult human head: implications of clinical near-infrared spectroscopy," *British Journal of Anaesthesia*, vol. 84, No. 1, pp. 38-42 (2000).
Zembrzuski, Cora, "Nutrition and Hydration," Best Practices in Nursing Care to Older Adults, The Hartford Institute for Geriatric Nursing, vol. 2, No. 2, Sep. 2000, 2 pages.
Attas, Michael, et al., "Visualization of cutaneous hemoglobin oxygenation and skin hydration using near-infrared spectroscopic imaging," *Skin Research and Technology*, vol. 7, pp. 238-245, (2001).
Bray, George A., et al., "Evaluation of body fat in fatter and leaner 10-y-old African American and white children: the Baton Rouge Children's Study," *Am J. Clin Nutr*, vol. 73, pp. 687-702 (2001).
Campbell, Wayne W., et al., "The Recommended Dietary Allowance for Protein May Not Be Adequate for Older People to Maintain Skeletal Muscle," *Journal of Gerontology*, vol. 56A, No. 6, pp. M373-M380 (2001).
Divert, Victor E., "Body Thermal State Influence on Local Skin Thermosensitivity," *International Journal of Circumpolar Health*, vol. 60, pp. 305-311 (2001).
Du, Y., et al., "Optical properties of porcine skin dermis between 900 nm and 1500 nm," *Phys. Med. Biol.*, vol. 46, pp. 167-181 (2001).

Endo, Yutaka, et al., "Water drinking causes a biphasic change in blood composition in humans," *Pflügers Arch—Eur J. Physiol*, vol. 442, pp. 362-368 (2001).
Garaulet, Marta, et al., "Site-specific differences in the fatty acid composition of abdominal adipose tissue in an obese population from a Mediterranean area: relation with dietary fatty acids, plasma lipid profile, serum insulin, and central obesity," *Am J. Clin. Nutr.*, vol. 74, pp. 585-591 (2001).
Haga, Henning A., et al., "Electroencephalographic and cardiovascular indicators of nociception during isoflurane anaesthesia in pigs," *Veterinary Anaesthesia and Analgesia*, vol. 28, pp. 126-131 (2001).
Kalantar-Zadeh, Kamyar, et al., "Near infra-red interactactance for Longitudinal Assessment of Nutrition in Dialysis Patients," *Journal of Renal Nutrition*, vol. 11, No. 1, pp. 23-31 (Jan. 2001).
Kamba, Masayuki, et al., "Proton magnetic resonance spectroscopy for assessment of human body composition," *Am J. Clin. Nutr.*, vol. 73, pp. 172-176 (2001).
Lever, M., et al., "Some ways of looking at compensatory kosmotropes and different water environments," *Comparative Biochemistry and Physiolog.*, vol. 130, Part A, pp. 471-486, (2001).
Mingrone, G., et al., "Unreliable use of standard muscle hydration value in obesity," *Am J. Physiol Endocrinal Metab.*, vol. 280, pp. E365-E371, (2001).
Šašic, Slobodan, et al., "Short-Wave Near-Infrared Spectroscopy of Biological Fluids. 1. Quantitative Analysis of Fat, Protein, and Lactose in Raw Milk by Partial Least-Squares Regression and Band Assignment," *Anal. Chem.*, vol. 73, pp. 64-71 (2001).
Schnickel, A.P., et al., "Evaluation of alternative measures of pork carcass composition," *J. Anim. Sci.*, vol. 79, pp. 1093-1119, (2001).
Sowa et al., "Near infrared spectroscopic assessment of hemodynamic changes in the early post-burn period," *Burns*, 27(3):241-9 (2001).
Troy, Tamara L., et al., "Optical properties of human skin in the near infrared wavelength range of 1000 to 2200nm," *Journal of Biomedical Optics*, vol. 6, No. 2, pp. 167-176 (Apr. 2001).
Tsukahara, K., et al., "Dermal fluid translocation is an important determinant of the diurnal variation in human skin thickness," *British Journal of Dermatology*, vol. 145, pp. 590-596 (2001).
Vescovi, Jason D., et al., "Evaluation of the BOD POD for estimating percentage body fat in a heterogeneous group of adult humans," *Eur J. Appl. Physiol.*, vol. 85, pp. 326-332 (2001).
Wang, Zimian, et al., "Magnitude and variation of ratio of total body potassium to fat-free mass: a cellular level modeling study," *Am J. Physiol. Endocrinal. Metab*, vol. 281, pp. E1-E7, (2001).
Watson, Walter, "Hydration of fat-free body mass: new physiological modeling approach," *Am J. Physiol. Endocrinol. Metab.*, Letters to the Editor, vol. 278, pp. E752-E753 (2001).
Attas, E. Michael, et al., "Near-IR Spectroscopic Imaging for Skin Hydration: The Long and the Short of It," *Biopolymers*, vol. 67, No. 2, pp. 96-106 (2002).
Attas, M. et al., "Long-Wavelength Near-Infrared Spectroscopic Imaging for In-Vivo Skin Hydration Measurements," *Vibrational spectroscopy* (Feb. 28, 2002), vol. 28, No. 1, p. 37-43.
Blank, T.B., et al., "Clinical Results from a Non-Invasive Blood Glucose Monitor," *Photonics West 2002 Meeting*, San Jose, California, Jan. 19-25, 2002 (25 pages).
Charney, Paul W., et al., "A new technique for establishing dry weight in hemodialysis patients via whole body bioimpedance," *Kidney International*, vol. 61, pp. 2250-2258 (2002).
Drobin, Dan, et al., "Kinetics of Isotonic and Hypertonic Plasma Volume Expanders," *Anesthesiology*, vol. 96, No. 6, pp. 1371-1380 (Jun. 2002).
Endo, Yutaka, et al., "Changes in Blood Pressure and Muscle Sympathetic Nerve Activity during Water Drinking in Humans," *Japanese Journal of Physiology*, vol. 52, pp. 421-427 (2002).
Haga, Henning A., et al., "Motor responses to stimulation during isoflurane anaesthesia in pigs," *Veterinary Anaesthesia and Analgesia*, vol. 29, pp. 69-75 (2002).
Klaus, Stephan, et al., "Assessment of fluid balance by measurement of skin tissue thickness during clinical anaesthesia," *Clin. Physiol. & Func. Im.*, vol. 22, pp. 197-201 (2002).

(56) References Cited

OTHER PUBLICATIONS

Meglinski, Igor V., et al., "Quantitative assessment of skin layers absorption and skin reflectance spectra simulation in the visible and near-infrared spectral regions," *Physiol. Meas.*, vol. 23, pp. 741-753, (2002).
Perez-de-Sá, Valéria, et al., "Mild Hypothermia Has Minimal Effects on the Tolerance to Severe Progressive Normovolemic Anemia in Swine," *Anesthesiology*, Vo. 97, pp. 1189-1197 (2002).
Ponec, Maria, et al., "Characterization of Reconstructed Skin Models," *Skin Pharmacol Appl Skin Physiol.*, vol. 15, Supplement 1, pp. 4-17, (2002).
Querleux, B., et al., "Anatomy and physiology of subcutaneous adipose tissue by in vivo magnetic resonance imaging and spectroscopy: Relationships with sex and presence of cellulite," *Skin Research and Technology*, vol. 8, pp. 118-124 (2002).
Van Bommel, Jasper, et al., "Intestinal and Cerebral Oxygenation during Severe Isovolemic Hemodilution and Subsequent Hyperoxic Ventilation in a Pig Model," *Anesthesiology*, vol. 97, No. 3, pp. 660-670 (Sep. 2002).
Wong, William W., et al., "Evaluating body fat in girls and female adolescents: advantages and disadvantages of dual-energy X-ray absorptiometry," *Am J. Clin Nutr.*, vol. 76, pp. 384-389 (2002).
Baković, Darija, et al., "Spleen volume and blood flow response to repeated breath-hold apneas," *J. Appl. Physiol.*, vol. 95, pp. 1460-1466 (2003).
Bartok, Cynthia, et al., "Measurement of nutritional statusin simulated microgravity by bioelectrical impedance spectroscopy," *J. Appl. Physiol.*, vol. 95, pp. 225-232 (2003).
Bouwstra, Joke A., et al., "Water Distribution and Related Morphology in Human Stratum Corneum at Different Hydration Levels," *J. Invest Dermatol*, vol. 150, pp. 750-758 (2003).
Butte, Nancy F., et al., "Composition of gestational weight gain impacts maternal fat retention and infant birth weight," *Am J. Obstet Gynecol*, vol. 189, pp. 1423-1432 (2003).
Cloonan, Clifford C., "Don't Just Do Something, Stand There!: To Teach of not to Teach, That is the Question—Intravenous Fluid Resuscitation Training for Combat Lifesavers," *The Journal of Trauma, Injury, Infection, and Critical Care*, vol. 54, No. 5, pp. S20-S25 (May Supplement 2003).
Cook, Lynda S., "IV Vluid Resuscitation," *Journal of Infusion Nursing*, vol. 26, No. 5, pp. 296-303 (Sep./Oct. 2003).
Dey, D.K., et al., "Body composition estimated by bioelectric impedance in the Swedish elderly. Development of population-based prediction equation and reference values of fat-free mass and body fat for 70- and 75-y olds," *European Journal of Clinical Nutrition*, vol. 57, pp. 909-916 (2003).
Farstad, M., et al., "Fluid extravasation during cardiopulmonary bypass in piglets—effects of hypothermia and different cooling protocols," *Acta Anaesthesiol. Scand.*, vol. 47, pp. 397-406 (2003).
Grandjean et al., "Hydration: issues for the 21$^{st}$ century", *Nutrition Reviews*, 61(8):261-271 (2003).
Heise, H.M., et al., "Reflectance spectroscopy can quantify cutaneous haemoglobin oxygenation by oxygen uptake from the atmosphere after epidermal barrier distruption," *Skin Research and Technology*, vol. 9, pp. 295-298 (2003).
Kasemsumran, Sumaporn, et al., "Simultaneous determination of human serum albumin, γ-globulin, and glucose in a phosphate buffer solution by near-infrared spectroscopy with moving window partial least-squares regression," *Analyst*, vol. 128, pp. 1471-1477 (2003).
Kemming, G.I., et al., "Hyperoxic ventilation at the critical haematocrit," *Resuscitation*, vol. 56, pp. 289-297 (2003).
Kurita, T., et al., "Comparison of isoflurane and propofol-fentanyl anaesthesia in a swine model of asphyxia," *British Journal of Anaesthesia*, vol. 91, No. 6, pp. 871-877 (2003).
Laaksonen, DE, et al., "Changes in abdominal subcutaneous fat water content with rapid weight loss and long-term weight maintenance in abdominally obese men and women," *International Journal of Obesity*, vol. 27, pp. 677-683 (2003).
Mao, Jinshu, et al., "Study of Novel Chitosan-gelatin artificial skin in vitro," *J. Miomed Mater Res.*, vol. 64, Part A, pp. 301-308 (2003).

Mauran, P., et al., "Renal and hormonal responses to isotonic saline infusion after 3 days' dead-down tilt vs. supine and seated positions," *Acta Physiol. Scand.*, vol. 177, pp. 167-176, (2003).
McHugh, Gerard, "Letter—Passive leg elevation and head-down tilt: effects and duration of changes," *Critical Care*, vol. 7, No. 3, p. 246 (Jun. 2003).
Meglinski, I.V., et al., "Computer simulation of the skin reflectance spectra," *Computer Methods and Programs in Biomedicine*, vol. 70, pp. 179-186, (2003).
Mendelsohn, Richard, et al., "Infrared microspectroscopic imaging maps the spatial distribution of exogenous molecules in skin," *Journal of Biomedical Optics*, vol. 8, No. 2, ppl 185-190 (Apr. 2003).
Mentes, Janet C., et al., "Reducing Hydration=-Linked events in Nursing Home Residents," *Clinical Nursing Research*, vol. 12, No. 3, pp. 210-225 (Aug. 2003).
Merritt, Sean, et al., "Coregistration of diffuse optical spectroscopy and magnetic resonance imaging in a rat tumor model," *Applied Optics*, vol. 42, No. 16, pp. 2951-2959 (Jun. 2003).
Parker, Lisa, et al., "Validity of Six Field and Laboratory Methods for Measurement of Body Composition in Boys," *Obesity Research*, vol. 11, No. 7, pp. 852-858 (Jul. 2003).
Petäjä L., et al., "Dielectric constant of skin and subcutaneous fat to assess fluid changes after cardiac surgery", *Physiological Measurement*, 24: 3383-390, 2003.
Rhodes, Andrew, et al., "Book Report—Haemodynamic monitoring in critically ill patients," *Critical Care*, vol. 8, p. 203 (2004).
Richardson, Andrew D., et al., "Multivariate analyses of visible/near infrared (VIS/NIR) absorbance spectra reveal underlying spectral differences among dried, ground confier needle samples from different growth environments," *New Phytologist*, vol. 161, pp. 291-301 (2003).
Ritz, Patrick, "Chronic Cellular Dehydration in the Aged Patient," Journal of Gerontology, vol. 56A, No. 6, pp. M349-M352 (2001).
Robinson, Martin P., et al., "A novel method of studying total body water content using a resonant cavity: experiments and numerical simulation," *Phys. Med. Biol.*, vol. 48, pp. 113-125, (2003).
Sergi, Giuseppe, et al., "Changes in Fluid Compartments and Body Composition in Obese Women after Weight Loss Induced by Gastric Banding," *Ann. Nutr Metab.*, vol. 47., pp. 152-157 (2003).
Wang, Zimian, et al., "Magnitude and variation of fat-free mass density: a cellular level body composition modeling study," *Am J. Physiol. Endocrinal. Metab*, vol. 284, pp. E267-E273 (2003).
Windberger, U, et al., "Whole blood viscosity, plasma viscosity and erythrocyte aggregation in nine mammalian species; reference values and comparison of data," *Exp., Physiol.*, vol. 88, No. 3, pp. 431-440 (2003).
Wolf, Martin, et al., "Absolute Frequency-Domain pulse Oximetry of the Brain: Methodology and Measurements," *Oxygen Transport to Tissue XXIV*, Chapter 7, Dunn and Swartz, Kluwer Academic/Plenum Publishers, pp. 61-73 (2003).
Ackland, G.L., et al., "Assessment of preoperative fluid depletion using bioimpedance analysis," *British Journal of Anaesthesia*, vol. 92, No. 1, pp. 134-136 (2004).
Arimoto et al., "Non-contact skin moisture measurement based on near-infrared spectroscopy", *Applied Spectroscopy*, 58(12):1439-1445 (2004).
Davidhizr, R., et al., "A review of the literature on how important water is to the world's elderly population," *International Nursing Review*, vol. 51, pp. 159-166 (2004).
Dullenkopf, A., et al., "Non-invasive monitoring of haemoglobin concentration in paediatric surgical patients using near-infrared spectroscopy," *Anaesthesia*, vol. 59, pp. 453-458 (2004).
Finlay, Jarod C., et al., "Hemoglobin oxygen saturations in phantoms and in vivo from measurements of steady-state diffuse reflectance at a single, short source-detector separation," *Medical Physics*, vol. 31, No. 7, pp. 1949-1959 (Jul. 2004).
Hendriks, F.M., et al., "Influence of hydration and experimental length scale on the mechanical response o human skin in vivo, using optical coherence tomography," *Skin Research and Technology*, vol. 10, pp. 231-241 (2004).
Hieda, I., et al., "Basic characteristics of the radio imaging method for biomedical application," *Medical Engineering & Physics*, vol. 26, pp. 431-437 (2004).

(56) References Cited

OTHER PUBLICATIONS

Ikizler, T. Alp, et al., "Urea space and total body water measurements by stable isotopes in patients with acute renal failure," *Kidney International*, vol. 65, pp. 725-732 (2004).

Isenring, E., et al., "Evaluation of foot-to-foot bioelectrical impedance analysis for the prediction of total body water in oncology outpatients receiving radiotherapy," *European Journal of Clinical Nutrition*, vol. 58, pp. 46-51 (2004).

Jacobi, Ute, et al., "In vivo determination of skin surface topography using an optical 3D device," *Skin Research and Technology*, vol. 10, pp. 207-214 (2004).

Kao, Bunsho, et al., "Evaluation of Cryogen Spray Cooling Exposure on In Vitro Model Human Skin," *Lasers in Surgery and Medicine*, vol. 34, pp. 146-154 (2004).

Kyle, Urusula G., et al., Bioelectrical impedance anslysis—part II: utilization in clinical practice, *Clinical Nutrition*, vol. 23, pp. 1430-1453 (2004).

Lof, Marie, et al., "Hydration of fat-free mass in healthy women with special reference to the effect of pregnancy," *Am J. Clin. Nutr.*, vol. 80, pp. 960-965 (2004).

Lowrie, Edmund G., "Urea space and body water," *Kidney Intl.*, vol. 66, No. 2, p. 868, Aug. 2004.

Mirrashed, F., et al., "Pilot study of dermal and subcutaneous fat structures by MRI in individuals who differ in gender, BMI, and cellulite grading," *Skin Research and Technology*, vol. 10, pp. 161-168 (2004).

Mirrashed, Fakhereh, et al., "In vivo morphological characterization of skin by MRI micro-imaging methods," *Skin Research and Technology*, vol. 10, pp. 149-160, (2004).

Notingher, Ioan, et al., "Mid-infrared in vivo depth-profiling of topical chemicals on skin," *Skin Research and Technology*, vol. 10, pp. 113-121, (2004).

Nouveau-Richard, S., et al., "In vivo epidermal thick ness measurement: ultrasound vs. confocal imaging," *Skin Research and Technology*, vol. 10, pp. 136-140, (2004).

Nuutinen, J., et al., "Validation of a enw dielectric device to assess changes of tissue water in skin and subcutaneous fat," *Physiol. Meas.*, vol. 25, pp. 447-454, (2004).

St-Onge, Marie-Pierre, et al., "Dual-energy X-ray absorptiometry lean soft tissue hydration: independent contributions of intra-and extracellular water," *Am J. Physiol. Endrocrinol Metab*, vol. 287, pp. E842-E847, Jul. 6, 2004.

Schou, A. J., et al., "Methodological aspects of high-frequency ultrasound of skin in children," *Skin Research and Technology*, vol. 10, pp. 200-206, (2004).

Stone, Darren A., et al., "Total body water measurements using resonant cavity perturbation techniques," *Phys. Med. Biol.*, vol. 49, pp. 1773-1788, (2004).

Takiwaki, Hirotsugu, et al., "Analysis of the absorbance spectra of skin lesions as a helpful tool for detection of major pathophysiological changes," *Skin Research and Technology*, vol. 10, pp. 130-135 (2004).

Van Kemenade, Patricia M., et al., "Do somotic forces play a role in the uptake of water by human skin?", *Skin Research and Technology*, vol. 10, pp. 109-112 (2004).

Wang, Zimian, et al., "Body cell mass: model development and validation at the cellular level of body composition," *Am J. Physiol. Endocrinol. Metab.*, vol. 286, pp. E123-E128 (2004).

Arimoto, Hidenobu, et al., "Depth profile of diffuse reflectance near-infrared spectroscopy for measurement of water content in skin," *Skin Research and Technology*, vol. 11, pp. 27-35 (2005).

Burmeister, J.J., et al., "Spectroscopic considerations for noninvasive blood glucose measurements with near infrared spectroscopy", *LEOS Newsletter*, vol. 12, No. 2, 1998, http://www.ieee.org/organizations/pubs/newsletters/leos/apr98/infrared.htm (last accessed, Nov. 30, 2005).

Haroun, D., et al., "Composition of the fat-free mass in obese and nonobese children: matched case—control analyses," *International Journal of Obesity*, vol. 29, pp. 29-36 (2005).

Ivorra, Antoni, et al., "Bioimpedance dispersion width as a parameter to monitor living tissues," *Physiol. Meas.*, vol. 26, pp. S165-S173 (2005).

Remote ICU Monitoring, *U.S. News & World Report*, pp. 45-61 (Aug. 1, 2005).

Sarkar, Shubho R., et al., "Assessment of Body Composition in Long-Term Hemodialysis Patients: Rationale and Methodology," *Journal of Renal Nutrition*, vol. 15, No. 1, pp. 152-158 (Jan. 2005).

Youcef-Toumi K., et al., "Noninvasive blood glucose analysis using near infrared absorption spectroscopy", MIT Home Automation and Healthcare Consortium, Progress Report No. 2-5, http://darbelofflab.mit.edu/ProgressReports/HomeAutomation/Report2-5/Chapter04.pdf (last accessed, Nov. 30, 2005).

García-Olmo, J., et al., "Advantages and disadvantages of multiple linear regression and partial least squares regression equations for the prediction of fatty acids," pp. 253-258 (undated).

Wang, Zimian, et al., "Cellular-Level Body Composition Model—A New Approach to Studying Fat-free Mass Hydration," *Annals New York Academy of Sciencei*, pp. 306-311 (undated).

Valleylab Products—LigaSure Vessel Sealing System, http://www.valleylab.com/product/vessel_seal/index.html, (last visited Nov. 21, 2007).

Valleylab Products—LigaSure Vessel Sealing Generator, http://www.ligasure.com/pages/generator.htm (last visited Nov. 21, 2007).

J. H. Ali, et al.; "Near Infrared Spectroscopy and Imaging to Prove differences in Water content in normal and Cancer Human Prostate Tissues," *Technology in Cancer Research & Treatment*, vol. 3, No. 5, Oct. 2004; pp. 491-497.

\* cited by examiner

SYSTEM AND METHOD FOR CONTROLLING TISSUE TREATMENT

BACKGROUND OF THE INVENTION

1. Field of the Invention

The present invention relates generally to tissue treatment during medical procedures. Specifically, the present techniques provide automated and manual systems for treating tissue while using spectroscopic techniques to monitor a tissue parameter.

2. Description of the Related Art

This section is intended to introduce the reader to various aspects of art that may be related to various aspects of the present invention, which are described and/or claimed below. This discussion is believed to be helpful in providing the reader with background information to facilitate a better understanding of the various aspects of the present invention. Accordingly, it should be understood that these statements are to be read in this light, and not as admissions of prior art.

Numerous techniques are used to treat or remove tissue during invasive and non-invasive medical procedures. Such techniques include the heat sealing of tissues and vessels, the freezing of tissues by cryoablation, and the removal of tissue or fluids by suction. These techniques all require a high degree of skill in administering the treatments in order to maximum the therapeutic efficacy.

For example, sealing of vessels during surgical procedures used to be performed by the use of fine stitches. However, stitches have a number of problems, including: a tendency to leak; the need to leave a foreign object in the body; and the time it takes for the surgeon to place the stitches. A more modern technique for sealing vessels is to administer heat to the walls of the vessel while holding the walls together under pressure. The heat partially melts the collagen in the walls of the vessel, while the pressure forces the melted collagen together to form a plastic seal. Although this technique is faster than stitching, less likely to leak, and leaves no foreign objects in the body, the energy must be carefully controlled to avoid damaging the surrounding tissues.

The heat may be generated in the tissue by the use of a radio frequency electrical current, which causes the tissues between two electrodes to heat and melt. The procedure may be controlled by monitoring the change in the impedance of the tissue between the electrodes, and lowering the energy administered as the changing impedance indicates that the sealing of the tissue is nearing completion. However, depending on various factors, including the conductivity of the surrounding tissues, a wider area may be exposed to the heat energy than is necessary for the treatment, potentially leading to undesirable damage.

Other techniques, such as cryoablation, may use thermocouples for monitoring the changes in the tissue during treatment. In cryoablation, a probe is connected to a refrigeration device and used to freeze tissues at the point of treatment. This freezing causes the formation of ice crystals in the cells, which ruptures the cell walls and causes the death of the frozen tissue. The practitioner may determine the area frozen by both the temperature and the appearance of the tissue. However, thermocouples may not accurately reflect the immediate temperature of the treated tissue either because of the time lag in the reading or the failure of probes to accurately determine extreme temperatures. As changes in the tissue may not be clearly visible, a larger area may be treated than is necessary for the therapeutic value obtained.

Still other techniques use a probe or needle connected to a suction device to remove tissue or fluids during medical procedures. An example of this technique may include, for example, liposuction, in which deposits of fat are removed from below the epidermis. Another common example involves draining fluids from the chest cavity, such as to relieve congestive heart failure or to remove fluid buildup from around the lungs after an injury. Suction techniques rely on the skill of the operator to ensure that the needle is located in the appropriate tissue type prior to activation of the suction device.

SUMMARY

Certain aspects commensurate in scope with the originally claimed invention are set forth below. It should be understood that these aspects are presented merely to provide the reader with a brief summary of certain embodiments that the invention might take and that these aspects are not intended to limit the scope of the invention. Indeed, the invention may encompass a variety of aspects that may not be set forth below.

An embodiment of the present techniques provides a system for controlling tissue treatment, comprising a tissue treatment device, and a spectroscopic tissue analyzer. The spectroscopic tissue analyzer is configured to analyze a parameter of a tissue and provide a feedback signal to control the tissue treatment device. In various aspects, the tissue treatment device may comprise a heat based tissue sealing device, a suction device for the removal of substances, or a tissue cryoablation unit.

Another embodiment of the present technique provides a method for controlling a tissue treatment device. The method comprises analyzing a parameter of a tissue using a spectroscopic tissue analyzer, and controlling the tissue treatment device using a feedback signal from the spectroscopic tissue analyzer. In one aspect, the feedback signal may be used to automatically control the tissue treatment device, while in another aspect, the system may alert the user, who may then choose how to control the tissue treatment device.

Another embodiment provides a probe for use in a medical procedure, comprising an optical system configured to deliver electromagnetic radiation to a tissue, another optical system configured to receive electromagnetic radiation from a tissue, and one or more active parts configured to treat tissue or remove substances. The active parts are disposed adjacent to the optical systems. In one aspect, this proximity allows for accurate control of the tissue treatment.

Another embodiment provides a method for making a system for tissue treatment, comprising making a system containing control circuitry, one or more emitters, one or more detectors, and one or more tissue treatment devices. The emitters are configured to send one or more wavelengths of electromagnetic radiation to a tissue. The detector elements are configured to detect the one or more wavelengths of electromagnetic radiation returned from the tissue and convert the detected electromagnetic radiation to one or more numerical parameters for the control circuitry. The control circuitry is programmed to analyze a parameter of the tissue from the one or more numerical parameters returned from the detectors, and to either automatically adjust the tissue treatment devices based on the parameter of the tissue, sound an audible alert to allow a user to adjust the tissue treatment device, or both.

Another embodiment provides a method for making a probe for treating tissue, comprising making a probe for delivering a tissue treatment to tissue adjacent to the tip of the probe, and attaching optical fibers to the outside of the probe. The optical fibers are configured to deliver electromagnetic radiation to a tissue adjacent to the tip of the probe and capture electromagnetic radiation from the tissue adjacent to the tip of the probe.

BRIEF DESCRIPTION OF THE DRAWINGS

Advantages of the invention may become apparent upon reading the following detailed description and upon reference to the drawings in which.

DETAILED DESCRIPTION OF SPECIFIC EMBODIMENTS

Figure 1:
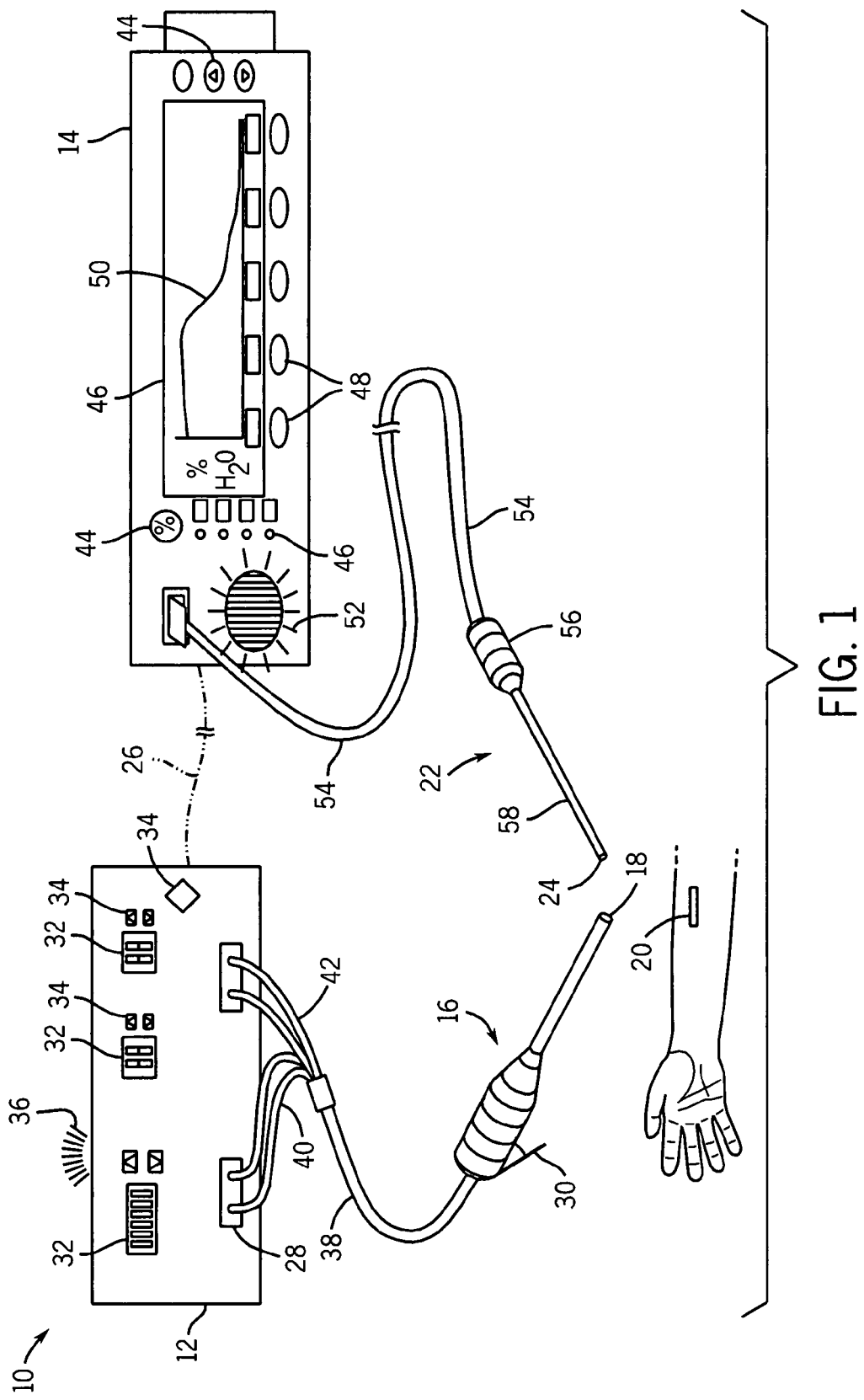
FIG. 1 is a perspective drawing of a tissue treatment device connected to spectroscopic tissue analyzer, which are connected to probes for administration of a tissue treatment and analysis of tissue parameter in accordance with an embodiment of the present techniques.

One or more specific embodiments of the present invention will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

I. Overview of Techniques

The present techniques include systems and methods that may be useful for controlling tissue treatment during medical procedures. The techniques use spectroscopic analysis to determine a parameter of the tissue, such as water content, as the tissue is being treated or prior to removal of the tissue. In some embodiments, the analysis may be performed on the tissue using one or more separate optical probes in close proximity to one or more probes administering the treatment. These techniques allow an operator to closely control the tissue treatment or removal process.

The techniques may use specially designed tissue treatment and spectroscopic analysis devices. Alternatively, commercial units may be retrofit with added communication components to allow control signals to be generated and received by each device from the other device. Further, the techniques may be implemented on a single unit containing both tissue treatment and spectroscopic analysis components.

The tissue parameter determined by the spectroscopic analysis may be used to automatically control the tissue treatment device, such as by reducing power as the tissue nears a final state. Alternatively, the tissue parameter may used to generate an alarm signal for a practitioner, allowing the practitioner to manually control the tissue treatment device as deemed appropriate.

The techniques discussed in detail below may be useful in various types of procedures in which spectroscopic analysis of a tissue parameter is incorporated in a single probe that also performs the tissue treatment. This proximity between treatment and analysis may result in improved control of a procedure. For example, in the heat sealing of vessels, it may be advantageous to analyze the composition of the tissue that is being held under pressure in a clamp. Further, in the removal of a tissue by suction, it may be useful to confirm the identity of the tissue at the tip of the probe prior to removal. Additionally, in the destruction of tissues by cryoablation, the determination of the concentration of ice present at the tip may improve control over the procedure.

II. A Tissue Treatment System

An exemplary tissue treatment system 10 in accordance with embodiments of the present techniques is shown in FIG. 1. In this tissue treatment system 10, a tissue treatment device 12 may be either manually or automatically controlled by the results of a analysis of a tissue parameter obtained from a spectroscopic tissue analyzer 14. The tissue treatment device 12 is connected to at least one tissue treatment probe 16 (e.g., tissue treatment probe 16A and tissue treatment probe 16B), which has an active tip 18 at which a tissue 20 may be treated. Further, the spectroscopic tissue analyzer 14 is connected to at least one optical probe 22, which has optics at the tip 24 for delivering electromagnetic radiation, such as light at infrared, near infrared, or visible wavelengths, to and from the tissue 20 under treatment. To control the procedure, the tissue treatment device 12 may be connected to the spectroscopic tissue analyzer 14 by a signal cable 26.

The tissue treatment device 12 may comprise devices that deliver energy to a tissue 20 or remove a tissue 20. In an exemplary embodiment, the tissue treatment device 12 may be a tissue sealing device using radio frequency (RF) energy for heating, such as the Ligasure™ vessel sealing system available from the Valleylab division of Tyco Healthcare Group LP. In another embodiment, the tissue treatment device 12 may be a suction device for the removal of fluids or tissues from the patient, such as the UltraSculpt system available from Mentor Medical Devices. In another embodiment, the tissue treatment device may be a cryoablation device for freezing and destroying diseased tissues, such as the cryogenic coolers available from BEI Medical (now Boston Medical). Those skilled in the art will recognize that other tissue treatment devices 12, such as laser ablation devices, may be used in embodiments of the present techniques while remaining within the scope of this disclosure.

Further, the tissue treatment device 12 may be specially designed for the system or may be a commercially available unit that has been retrofit to allow for operation under the control of a spectroscopic tissue analyzer 14. The retrofitting may involve the addition of communications components to allow connection to the signal cable 26. Programming modifications may then allow the tissue treatment to be controlled by a signal received from the spectroscopic tissue analyzer 14. Such a signal may be used, for example, to activate the tissue treatment, deactivate the tissue treatment, or change the intensity of the treatment, as discussed with respect to FIGS. 4 and 5, below. Alternatively, the signal cable 26 may be connected to an existing external control interface on a commercially available tissue treatment device 12, such as a switch plug 28. Control of the unit by the spectroscopic tissue analyzer 14 may be in addition to, or instead of, manual activation through an external device, such as a switch 30 that may be located on the tissue treatment probe 16.

The tissue treatment device 12 may include one or more displays 32 and one or more controls 34 to allow display of and/or control over tissue treatment settings. Such displayed settings may include the current values of, or preset limits for, energy intensity levels, treatment duration, or treatment efficacy, among others. The tissue treatment device 12 may also include an audible alarm 36 that may be used either independently of, or in conjunction with, alerts from the spectroscopic tissue analyzer 14. The feedback from the displays 32 and audible alarm 36 of the tissue treatment device 12 may be useful as failsafe alerts in case changing conditions interfere with the spectroscopic analysis of the tissue parameter, and, thus, the control by the spectroscopic tissue analyzer 14.

The tissue treatment device 12 is connected to the tissue treatment probe 16 by a probe cable 38. The probe cable 38 may contain one or more control cables 40, which may be connected to a switch 30 that may be located on the probe body. The signal from this switch 30 may be used for activation of the tissue treatment device 12. Additionally, the signal may be sent to the spectroscopic tissue analyzer 14 over the control cable 26 for activation of the tissue treatment system 10, as discussed in detail below. The probe cable 38 may contain cables or tubing 42 for administration of the tissue treatment, such as RF cables for a vessel sealing system or suction tubing for a suction device.

As in the case of the tissue treatment device 12, the spectroscopic tissue analyzer 14 may be specially designed for application in the tissue treatment system 10 or may be a commercial unit adapted for use in the system. For example, it may be an oximeter-like device used to measure tissue hydration according to techniques disclosed in the references discussed below. Alternatively, the spectroscopic tissue analyzer 14 may use other spectroscopic techniques to measure other parameters such as tissue type, tissue temperature, or the concentration of ice versus water.

The spectroscopic tissue analyzer 14 may have controls 44 and displays 46 for the entry and display of analysis and control settings specific to the spectroscopic tissue analyzer 14. The controls 44 on the spectroscopic tissue analyzer 14 may also be used to enter settings for the tissue treatment device 12. For example, in addition to treatment intensity or duration, as required for the tissue treatment device 12, such settings may include the specific type of analysis desired, the wavelengths for the analysis, the probe types, treatment control settings, or analysis settings. Programmable keys 48 with legends displayed on the screen (so called "softkeys") may be convenient due to the complexity and range of the settings needed for the tissue treatment system 10.

Results 50 of the analysis of the tissue parameter may be shown on the display 46 or presented by an audible signal 52. Such results 50 may include tissue water content, tissue lipid content, tissue temperature or other parameters related to the tissue treatment. The audible signal 52 may be in the form of one or more alarm tones or may be an annunciation of the results by a voice synthesizer. In addition to displaying the results 50, the spectroscopic tissue analyzer 14 may send one or more signals to the tissue treatment device 12 through the control signal line 26. These signals may trigger the tissue treatment device 12 to start the tissue treatment, change the power of the tissue treatment, or terminate the tissue treatment, as discussed with respect to FIG. 4, below.

Although the above descriptions of the tissue treatment device 12 and the tissue analyzer 14 have detailed some possible operational settings that may be entered or results that may be displayed, those skilled in the art will recognize that the specific settings and results will depend on the type of analysis and tissue treatment implemented.

The spectroscopic tissue analyzer 14 has an optical probe 22 attached by an optical probe cable 54. Generally, the probe 22 must carry light from one or more emitters to the tissue under treatment, and return the light to one or more detectors for conversion to an electrical signal. In one embodiment, the emitters and detectors may be located in the spectroscopic tissue analyzer 14, in which case the cable 54 may contain fiber optic bundles to transmit light from the spectroscopic tissue analyzer 14 to the optical probe tip 24. In another embodiment, the emitters and detectors may be located in the handle 56 of the optical probe 22 and the cable 54 will contain electrical lines to carry signals to and from the probe 22. In this embodiment, the emitters and detectors in the handle may be coupled to the optics at the tip 24 of the optical probe 22 via optical fibers inside the probe body 58. In other embodiments, the probe tip 24 may have integrated emitters and detectors.

The selection of emitters and detectors may depend on the location chosen for the optics. In embodiments having the emitters and detectors in the probe, the emitters may be small light emitting diodes (LEDs), which have specific wavelengths at which light is emitted. The use of LEDs may minimize the need for wavelength filters, monochromators, or other bulky devices to narrow the wavelength distribution, allowing the optics to be in the probe handle. The selection of the specific LEDs, and, thus, the wavelengths, may be made on the basis of factors such as the tissue parameters, the analytical techniques, the need to eliminate noise interference, or the need to eliminate temperature interference. Such factors are discussed in more detail below with respect to analyzing for tissue water content.

Similarly, in embodiments having detectors in the probe, the detectors may be photodiodes, phototransistors, or any other device that has an appropriate size and the necessary sensitivity at the desired wavelengths. In contrast, in embodiments having the optics in the spectroscopic tissue analyzer 14, the size of the emitters and detectors may be less important. In these embodiments, more general light emitters may be used with filters or monochromators for selection of specific wavelengths. Such light emitters may include incandescent lamps, arc lamps, or other broad spectrum sources. Detectors that may be used in these embodiments may include those listed above, as well as photomultiplier tubes or other large, highly sensitive detectors.

III. A Combined Unit for Tissue Treatment

Figure 2:
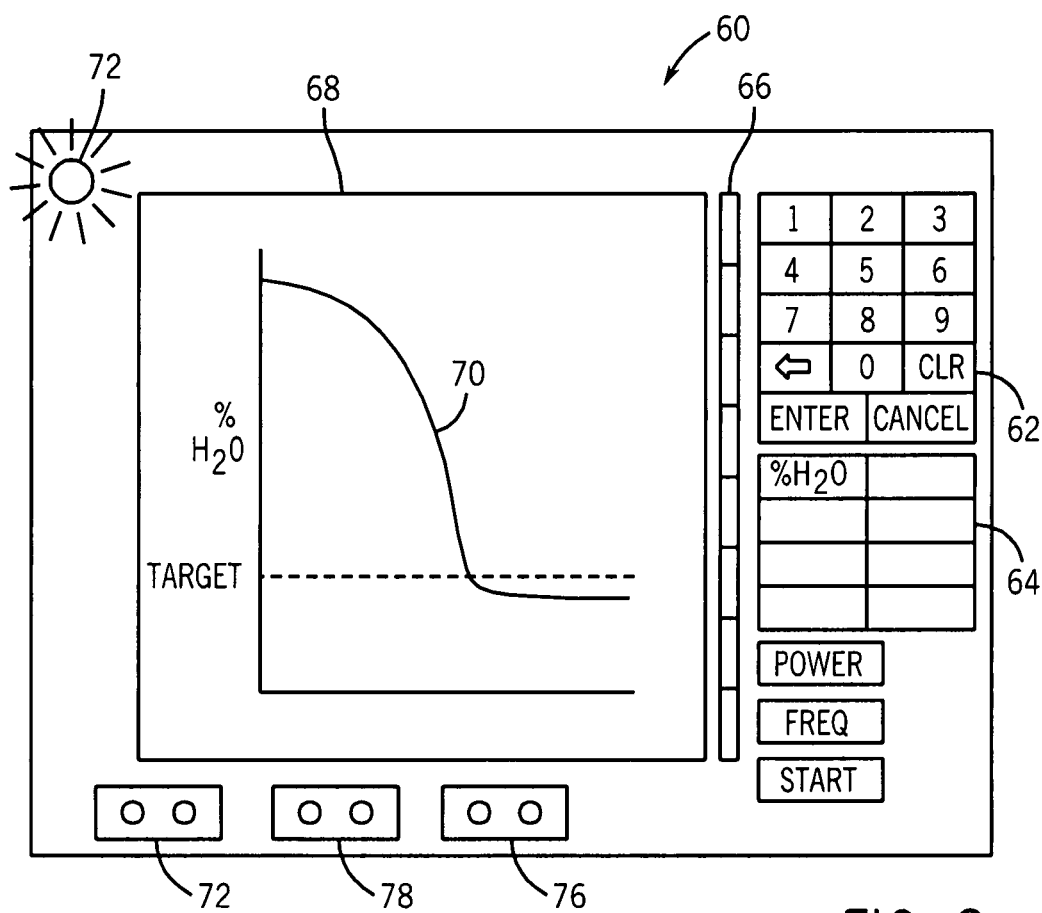
FIG. 2 is a front view of a single unit that integrates both a tissue treatment function and a spectroscopic tissue analysis function in accordance with an embodiment of the present techniques.

While the current techniques may be implemented using a separate tissue treatment device 12 and spectroscopic tissue analyzer 14, other embodiments may have a single unit that combines both functions. A front view of such a combined unit 60 is shown in FIG. 2. As shown in this figure, the combined unit 60 may have controls, such as a keypad 62, function keys 64, and programmable softkeys 66, among others, and a display 68. The controls and display allow entry of operational settings for both the analysis and tissue treatment, as discussed above with respect to the spectroscopic tissue analyzer 14 and tissue treatment device 12. The results 70 of the analysis of the tissue parameter may be shown on the display 68 of the combined unit 60. Additionally, an audible alarm 72 may be used to alert the practitioner of the results from this analysis. In embodiments of the present techniques, this alarm 72 may be tones indicating when targets are reached, or may be a voice annunciation of the results of the analysis of the tissue parameter.

The combined unit 60 may also have all of the connectors needed to interface with the probes 16 and 22. Such connectors may include a plug 72 for the cables or tubing 42 needed for the tissue treatment, a plug 76 for the optical probe cables 54, and a plug 78 for the control switch cables 40.

IV. Algorithms for Determining Tissue Parameters

The techniques discussed above may be further clarified by examining algorithms that may be used to determine tissue parameters during treatment in accordance with embodiments of the present techniques. These algorithms may be implemented on the tissue treatment system 10, discussed above. In one embodiment, a vessel, such as a blood or lymph vessel, may be heat sealed using energy from a radio frequency (RF) generator. During this procedure, the water content of the tissue may be monitored to determine the progress of the treatment. In another embodiment, the lipid content of a tissue may be determined in order to identify the type of tissue prior to removal by a suction device. In another embodiment, the percent content of water that has been converted to ice crystals may be determined to identify frozen tissue during a cryoablation procedure.

A. The Determination of Tissue Water Content

Various spectroscopic tissue analysis techniques may be used in embodiments to determine the progress in heat sealing a tissue, including techniques such as determining the rearrangement of the proteins as they are denatured during the sealing process. However, the most relevant tissue parameter may be the water content of the tissue, as the water content of the tissue is known to decrease in a predictable fashion during the sealing procedure. The use of spectrophotometric means for measuring and calculating fluid metrics, such as water content of tissue, are described in U.S. Pat. No. 6,591,122. Additionally, U.S. Pub. No. 2003-0220548, U.S. Pub. No. 2004-0230106, U.S. Pub. No. 2005-0203357, U.S. patent application Ser. No. 11/528,154, U.S. Pat. App. No. 60/857045, U.S. patent application Ser. Nos. 11/283,506, and 11/282,947 discuss methods for measuring and calculating fluid metrics. The techniques, methods and apparatuses disclosed in the aforementioned patents, publications and applications may be implemented in particular embodiments of the present invention. As such, each of the aforementioned patents, publications and applications are incorporated herein by reference.

The fluid metrics computed by the above mentioned references typically have correlated a local measurement to a whole body water value. Spectrophotometric means, however, may also be used in calculating a local fluid measurement. Specifically, similar measurements, such as the ratio of water-to-water and other constituents, may be taken but the data may be interpreted to indicate a local fluid metric rather than a whole body fluid metric. The local fluid metric may then be used for the determination of the changes in a tissue as a treatment procedure progresses, as will be discussed in detail below.

The percent water component of most organs in the human body is 50-80%, whereas the percent water component of skin is approximately 70% and the water percentage of the lungs is approximately 95%. A significant amount of this water may be lost from the tissue during a sealing procedure. For example, the water content of a vessel may drop by around 30% as the vessel is sealed. This loss in water content correlates to the formation of the plastic seal, so it may be used for the determination of the sealing endpoint, e.g., the point at which the application of the RF energy, or other treatment, should be stopped before adjacent tissues are harmed.

In an exemplary embodiment, the water content, expressed as a water fraction, $f_w$, may be estimated based on the measurement of reflectances, $R(\lambda)$, at three wavelengths (e.g., $\lambda_1$=1190 nm, $\lambda_2$=1170 nm and $\lambda_3$=1274 nm) and the empirically chosen calibration constants $c_0$, $c_1$ and $c_2$ according to the equation:

$$f_w = c_2 \log[R(\lambda_1)/R(\lambda_2)] + c_1 \log[R(\lambda_2)/R(\lambda_3)] + c_0 \tag{1}$$

In an alternative exemplary embodiment, the water fraction, $f_w$, may be estimated based on the measurement of reflectances, $R(\lambda)$, at three wavelengths (e.g., $\lambda_1$=1710 nm, $\lambda_2$=1730 nm and $\lambda_3$=1740 nm) and the empirically chosen calibration constants $c_0$ and $c_1$ according to the equation:

$$fw = c_1 \frac{\log[R(\lambda_1)/R(\lambda_2)]}{\log[R(\lambda_3)/R(\lambda_2)]} + c_0. \tag{2}$$

Total accuracy in the determination of tissue water content of better than ±0.5% can be achieved using Equation (2), with reflectances measured at the three closely spaced wavelengths.

In another embodiment, tissue water fraction, $f_w$, is estimated according to the following equation, based on the measurement of reflectances, $R(\lambda)$, at a plurality of wavelengths:

$$fw = \frac{\left[\sum_{n=1}^{N} p_n \log\{R(\lambda_n)\}\right] - \left[\sum_{n=1}^{N} p_n\right] \log\{R(\lambda_{N+1})\}}{\left[\sum_{m=1}^{M} q_m \log\{R(\lambda_m)\}\right] - \left[\sum_{m=1}^{M} q_m\right] \log\{R(\lambda_{M+1})\}}, \tag{3}$$

where $p_n$ and $q_m$ are calibration coefficients. Equation (3) provides cancellation of scattering variances, especially when the N+1 wavelengths are chosen from within the same band (i.e. 950-1400 nm, 1500-1800 nm, or 2000-2300 nm).

The careful selection of wavelengths may be used to overcome a number of problems that may affect accurate analysis of tissue parameter. For example, selection of wavelength pairs having matched absorbance by water, i.e., water absorbance coefficients, may yield estimates of water fraction that are essentially insensitive to scattering variations. The matched absorbances ensure that the lengths of the optical paths through the tissue at the wavelengths at which the reflectances are measured may be substantially matched.

Further, as tissue treatment often involves extremes of temperature at the point of treatment, it may be important to compensate for temperature variations to ensure an accurate measurement. Proper selection of wavelengths may be used to compensate for temperature variations by a number of techniques. For example, in one embodiment the wavelength sets may be chosen to be close to temperature isobestic wavelengths in the water absorption spectrum. As the isosbestic points are points at which the absorbance spectrum does not change with temperature, the use of these points may yield water fraction measurements that also do not change with temperature. For example, the wavelength pair of 1180 and 1300 nm is a pair of exemplary isosbestic wavelengths in the water absorption spectrum.

In another embodiment, the amount of the temperature shift in the absorbances is measured and modeled. The model may then be used by the algorithms to mathematically cancel the temperature shift in the absorbance when optical measurements are combined to compute the value of the tissue water content.

B. The Determination of Lipid Content

Similar algorithms to those discussed above for determining tissue water content may be implemented for the determination of lipid content in tissue. Such algorithms may be useful for identifying fat tissue prior to removal using a suction based tissue treatment device. For example, human fat, or adipose, tissue has a lipid content of around 87%. In contrast, lean muscle may have a lipid concentration of 5%, or less.

Algorithms for the determination of lipid content take advantage of the fact that spectral peaks for lipids may be found at different wavelengths from those used in the determination of tissue water content. For example, lipids have a peak absorbance at around a wavelength of 1250 nm. The volume fraction scaled absorbance for all three major components of tissue, i.e., water, lipids, and proteins, is approximately equal at around 1185 nm. Numerical simulations have indicated that accurate measurement of the lean tissue water content, $f_w$, can be accomplished using Equation (2) by combining reflectance measurements at 1125 nm, 1185 nm and 1250 nm. As the lean tissue water content is calculated by compensating for lipid content of the tissue, this algorithm may also be used to directly analyze for lipid content in embodiments. For example, if using $\lambda_1=1125$ nm, $\lambda_2=1185$ nm and $\lambda_3=1250$ nm run in Equation (2) gives lean tissue water content, then the use of $\lambda_1=1250$ nm, $\lambda_2=1185$ nm and $\lambda_3=1125$ nm may allow the lipid content to be determined.

C. The Determination of Frozen Tissue

In cryoablation, extremely cold temperatures are used to freeze diseased tissues. The freezing process forms ice crystals in the cells of the tissue, which lacerate the cell membrane, rupturing the cell. The ruptured cells may be removed by the practitioner during the procedure or may be reabsorbed by the body after the procedure ends. The freezing process is performed using a cryoprobe, which is connected to a cryogenic refrigeration unit. The quantification of frozen tissue of or the determination of tissue temperature may allow control of the procedure in various embodiments.

The most effective spectral algorithm for controlling a cryoablation procedure may be based on identifying and quantifying the degree of frozen tissue using the spectral differences between water and ice. The algorithms would be generated by identifying appropriate wavelengths for the measurement, then calibrating the response of the reflectances based on animal models. This calibration may be used to generate coefficients for use in Equations (1)-(3) above. The measured reflectances would be used in these Equations to determine the percent concentration of ice crystals in a tissue sample. While complex, those skilled in the art will recognize that the calibration procedure is relatively straightforward.

Another algorithm that may be used to control such procedures may take advantage of the temperature dependent spectral shifts of the water peaks in the NIR, as discussed above, to determine the temperature of the tissue. The spectral shifts may be modeled as described for the temperature compensation calculation of the tissue water content analysis.

V. Spectroscopic Control of Tissue Treatment

Figure 3:
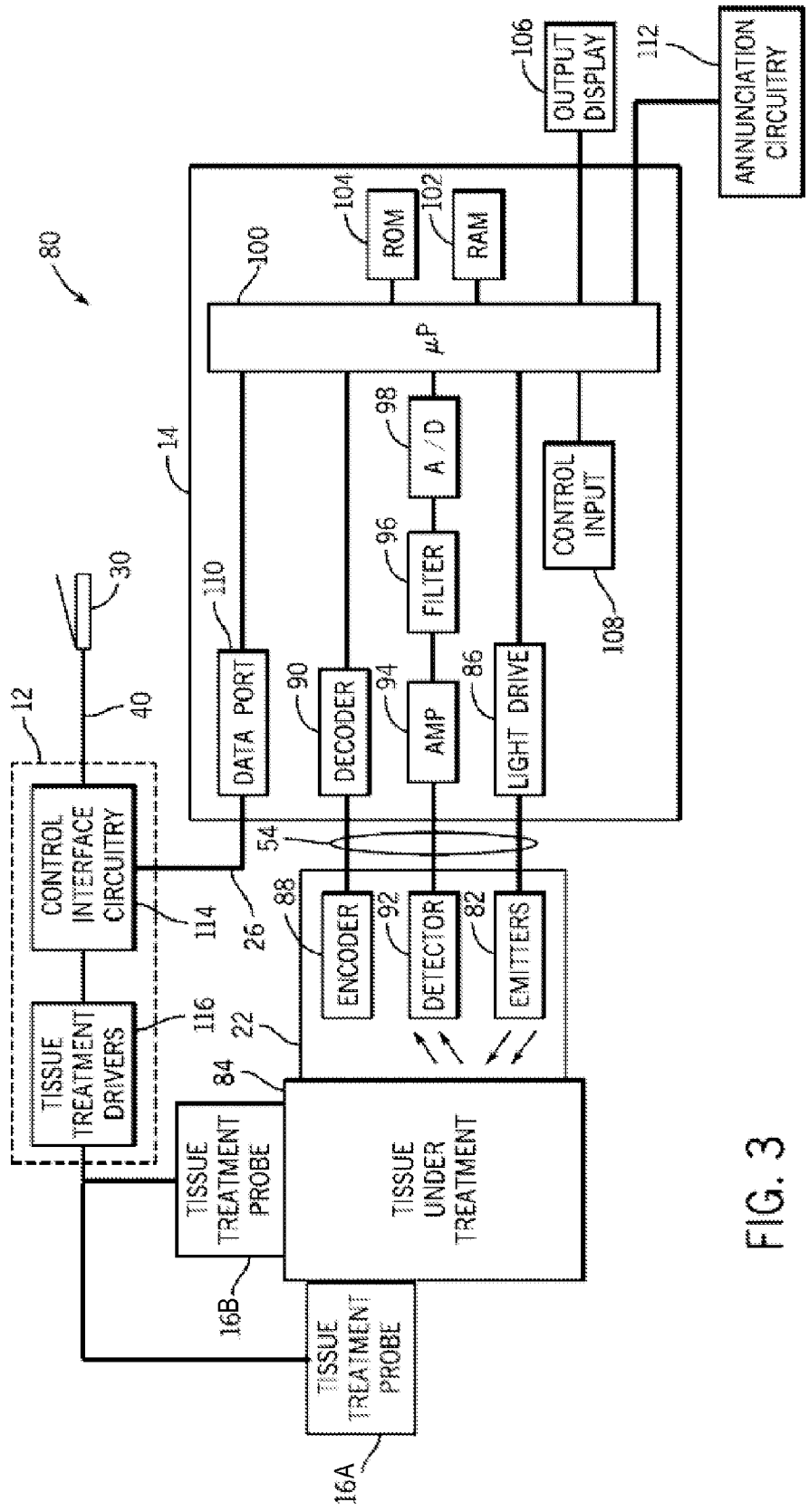
FIG. 3 is a block diagram showing the components of a system that may have both a tissue treatment device and a spectroscopic tissue analyzer in accordance with embodiments of the present techniques.

In embodiments of the present techniques, the algorithms discussed above may be implemented in a spectrophotometric device for determination of tissue treatment progress, such as, for example, in the system 10 discussed with respect to FIG. 1. The use of spectroscopic methods provides the advantage of fast detection, allowing tissue treatment to be stopped before damage to surrounding tissues occurs. An example of a spectrophotometric device which may be used in embodiments for control of tissue treatment is shown in FIG. 3. This is a block diagram of an implementation of an exemplary tissue treatment system 80. The tissue treatment system 80 may comprise the separate units of the tissue treatment system 10, discussed with respect to FIG. 1, or the combined unit 60, discussed with respect to FIG. 2.

In this example, the tissue treatment system 80 has an optical probe 22 having at least one emitter 82 configured to transmit light into the tissue of a patient 84. Embodiments may use two, three, or more emitters depending on the number of absorbance signals required for the particular algorithm selected as discussed above with respect to Equations (1), (2), and (3). In some embodiments, the emitters may directly transmit light into the tissue, while in other embodiments, the emitters may be coupled to optical fibers which carry the light to the tissue.

A light drive unit 86 in the spectroscopic tissue analyzer 14 controls the timing of the emitters 82. While the emitters 82 are manufactured to operate at one or more certain wavelengths, variances in the wavelengths actually emitted may occur which may result in inaccurate readings. To help avoid inaccurate readings, an encoder 88 and decoder 90 may be used to calibrate the spectroscopic tissue analyzer 14 to the actual wavelengths being used. The encoder 88 may be a resistor, for example, whose value corresponds to coefficients stored in the spectroscopic tissue analyzer 14. The coefficients may then be used in the algorithms. Alternatively, the encoder 88 may also be a memory device, such as an EPROM, that stores information, such as the coefficients themselves. Once the coefficients are determined by the spectroscopic tissue analyzer 14, they are inserted into the algorithms in order to calibrate the tissue treatment device 80.

The light from the emitters 82 is scattered and absorbed by the various constituents of the tissue, such as water and protein. The optical probe 22 contains at least one detector 92 configured to detect the scattered and reflected light and to generate a corresponding electrical signal. As discussed above for the emitter 82, the detected light may be carried from the probe tip 24 to the detector 92 by optical fibers. Alternatively, the light may be directly received from the tissue by the detector.

The detected signal from the detector 92 is carried from the optical probe 22 to a spectroscopic tissue analyzer 14 by a spectroscopic probe cable 54. In the spectroscopic tissue analyzer 14, the detected signals are amplified and filtered by amplifier 94 and filter 96, respectively, before being converted to digital signals by an analog-to-digital converter 98. The analog-to-digital converter 98 is connected to a microprocessor 100 for further processing of the digital signals.

The microprocessor 100 is connected to other component parts of the spectroscopic tissue analyzer 14, such as a RAM 102, a ROM 104, a display 106, control inputs 108, and a data port 110. The RAM 102 stores the signals from the analog-to-digital converter 98 for use in the algorithms used to compute the fluid levels or metrics. The algorithms are programmed into ROM 104, and may include algorithms designed to implement Equations 1, 2, or 3, above. Alternatively, the algorithms may be related to other types of tissue treatment, such as, for example, algorithms for tissue type identification prior to removal by a suction unit or algorithms to distinguish between frozen and unfrozen tissue, as discussed above.

The spectroscopic tissue analyzer 14 may be configured to display the calculated tissue parameters on display 106. The display 106 may simply show the calculated fluid measurements for a particular region of tissue where the sensor has taken measurements. The fluid measurements may be represented as a ratio or a percentage of the water or other fluid present in the measured tissue. As the ratio or percentage may not have any particular significance to a practitioner, the spectroscopic tissue analyzer 14 may be programmed to correlate the ratio or percentage to a number indicative of the progress in sealing the tissue. For example, a zero may be shown on the display 106 when the tissue treatment is started. The displayed number is incremented as the treatment progresses. Once the treatment is completed, a 100 may be shown on the display 106, indicating that the treatment is completed and further treatment could damage surrounding tissue. Alternatively, an annunciation or alarm circuit 112 may be used to inform the practitioner of the treatment progress. This may have the advantage of alerting the practitioner without requiring that he or she watch the display 106 instead of the tissue 84. Regardless of the manner of presentation, the objective is to present the fluid metric information to a practitioner in a manner that may be quickly and easily understood.

In a more complex system, the display 106 may show a graphical image illustrating the fluid measurements or fluid ratios across an area, such as in the immediate vicinity of the treatment probe. Regions may be shaded or color coded to indicate relative fluid levels or fluid ratios. For example, normal fluid levels or fluid ratios indicating unaffected tissues may be indicated by presenting the region with a green hue on the display 106. Alternatively, regions of tissue that have been affected by the treatment and deviate from a normal fluid level or fluid ratio may be indicated by coloring the region a reddish hue, for example. As the fluid level or fluid ratio may change across an area being measured, the differences in the fluid ratio may be shown by the shading or coloring technique. Indeed, a single graphical image may demonstrate a wide range of shades or hues corresponding to the fluid ratio of a particular region. Such an output display would be advantageous in determining exactly what area has been affected by the tissue treatment. In one embodiment, the mapping may be used to map tissue water content to determine tissue affected during a heat sealing procedure. In another embodiment of the present invention, such a graphical display may be used to map tissue temperature or the extent of tissue frozen during cryoablation.

The control inputs 108 allow a practitioner to interface with the spectroscopic tissue analyzer 14. For example, if a particular spectroscopic tissue analyzer 14 is configured to detect tissue water composition during a heat sealing procedure, a practitioner may input or select settings, such as tissue type, target water composition, or baseline fluid levels for the tissue that is to be measured, among others. Other setting may be useful for other types of tissue treatment. For example, in the suction removal of a tissue, the percentage of lipids in the target and non-target tissues may be entered.

Specifically, baseline settings associated with various types of tissues may be stored in the spectroscopic tissue analyzer 14 and selected by a practitioner as a reference level for determining the end point for the treatment. Additionally, patient data may be entered, such as weight, age and medical history data. This information may be used to validate the baseline measurements or to assist in the understanding of anomalous readings. For example, severe artheroslerosis may alter the baseline reading of vessel water content and, therefore, may affect the determination of the end point for the heat sealing.

In addition to displaying the results of the analysis of the tissue parameter, the spectroscopic tissue analyzer 14 may be used to automatically control tissue treatment. To facilitate this control, a tissue treatment device 12 may be connected to the spectroscopic tissue analyzer 14 through a signal cable 26 connected to a data port 110 built into the spectroscopic tissue analyzer 14. The tissue treatment device 12 has control and interface circuitry 114 to control the tissue treatment drivers 116 based on the signal received from the spectroscopic tissue analyzer 14, as discussed with respect to FIG. 4, below. The tissue treatment drivers 116 are connected to a tissue treatment probe 16, which is placed in contact with the tissue under treatment 84. A switch 30 connected to the external tissue treatment device 12 by a cable 40 activates the tissue treatment. This switch may also activate the tissue treatment system 80.

Figure 4:
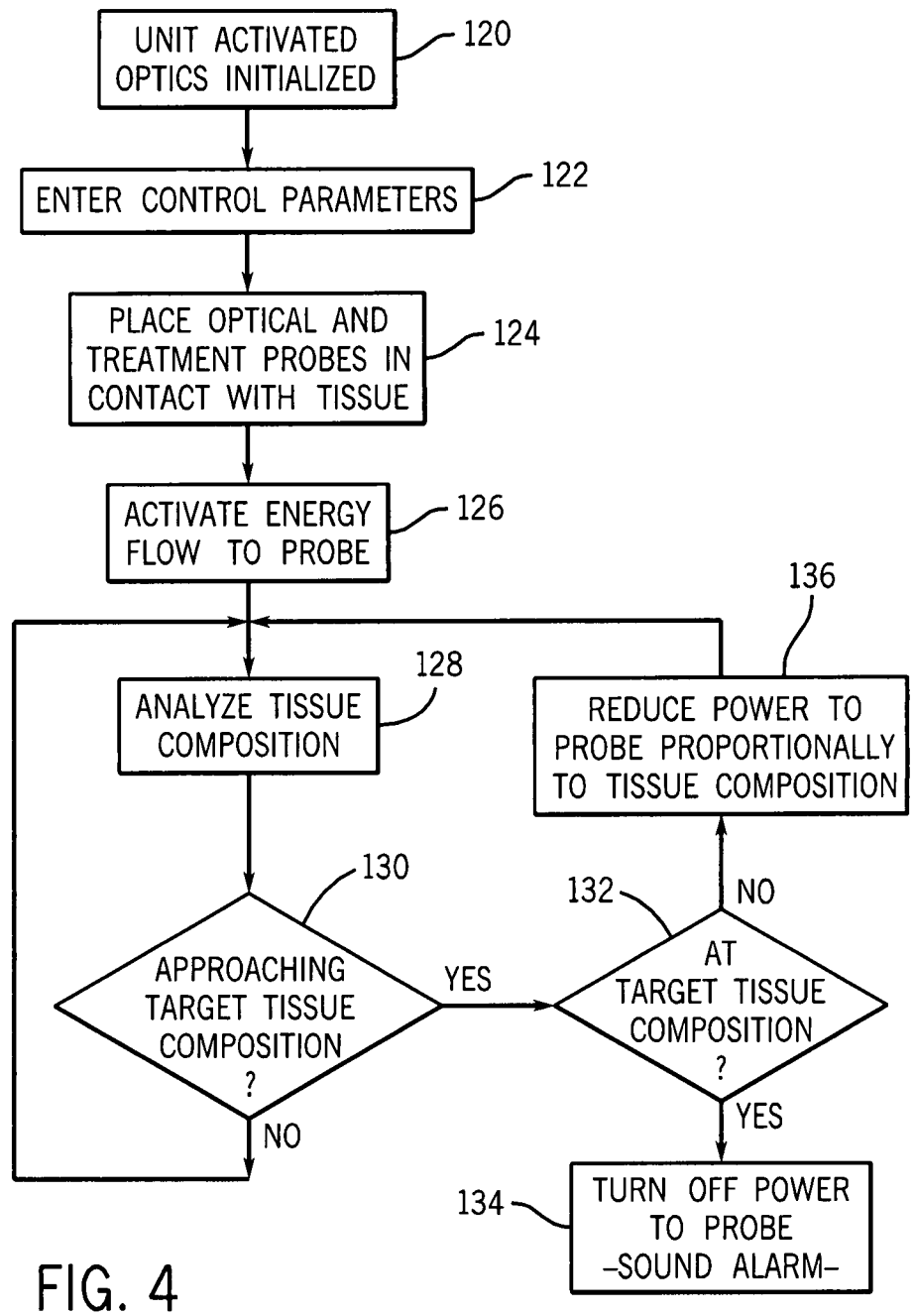
FIG. 4 is a flowchart showing a process for automated control of a tissue treatment device in accordance with embodiments of the present techniques.
Figure 5:
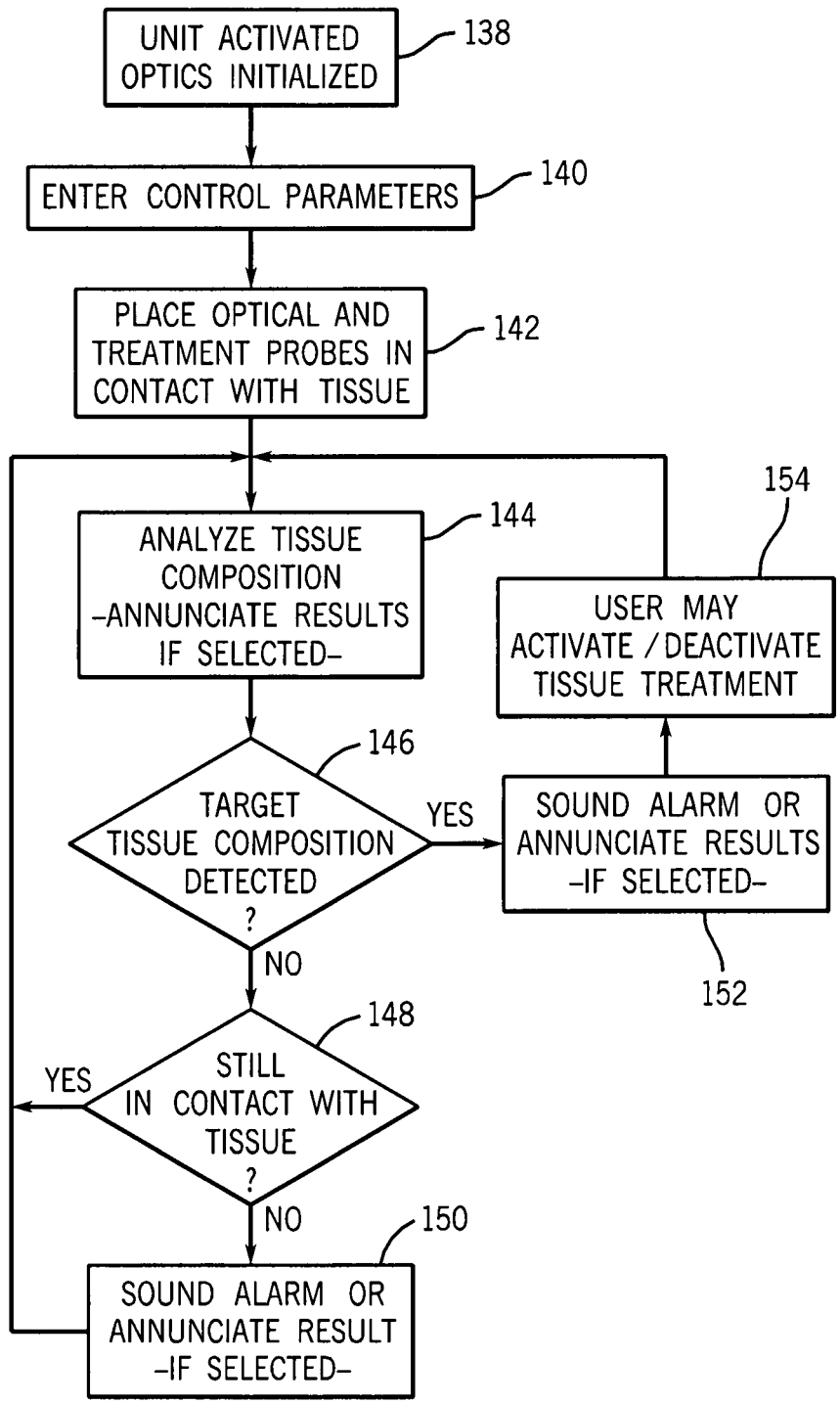
FIG. 5 is a flowchart showing a process for manual control of a tissue treatment device in accordance with embodiments of the present techniques.

The use of the spectroscopic tissue analyzer 14 for controlling a tissue treatment device 12, as described above, is further clarified by examining the sequence of operations that may be used in different embodiments. While continuing to refer to FIG. 3, block diagrams illustrating exemplary automatic and manual operational sequences are shown in FIGS. 4 and 5. These examples merely illustrate two possible embodiments, and are not intended to be limiting.

A. Automatic Control of Tissue Treatment

As shown in FIG. 4, a tissue treatment procedure under automatic control begins when the practitioner powers the unit, as shown in block 120, which initializes the optics, network connections, and other circuits. The practitioner enters the settings for the tissue treatment, as shown in block 122. Such settings may include patient specific information, such as age or weight, power levels for the treatment, duration of the treatment, tissue types, alarm modes, and annunciation settings, among others. When the system is utilized during the medical procedure, the practitioner places the tissue treatment probe 16 and the optical probe 22 in contact with a target tissue 84, as shown in block 124. As shown in block 126, the practitioner then starts the energy flow to the probe, for example, by pressing the switch 30, which may be located on the tissue treatment probe 16. This also activates the automated sequence for controlling the tissue treatment. For example, if the device is intended to seal a vessel, RF energy is sent to the tissue treatment probe at full power to heat the tissue.

The system then enters an automated control mode, which begins with the spectroscopic analysis of a parameter of the tissue located under the optical probe 22, as shown in block 128. In some embodiments, the spectroscopic analysis may use algorithms to determine the tissue water content to control the heat sealing of a vessel, as discussed above. In other embodiments, the spectroscopic analysis may use algorithms to determine lipid concentration to identify fat tissue, prior to removing the tissue with a suction device. While in other embodiments, spectroscopic techniques may be used to identify quantify the ice content of tissue to control a cryoablation procedure.

After analyzing for the tissue parameter in block 128, the system determines if the parameter lies within a previously selected range of the target value, as shown in block 130. In embodiment in which a vessel is heat sealed using RF energy, this parameter may be a value for tissue water content that is within a certain percentage of the final value for water content. Such a preset point may allow for early reductions in power to the RF probe, resulting in less damage to surrounding tissues. In other embodiments, such as for removing a tissue with a suction device, the range may be used to improve the response of a tissue treatment device 12 while the probe tip 24 is in the presence of mixtures of cells, such as the boundary between fat and muscle. In another embodiment, such as in cryoablation, the parameter may be the allowable ice concentration in the tissue that will not result in significant tissue damage.

If the parameter of the tissue is not within the selected range of the target, the system may leave tissue treatment settings unchanged, returning to block 128 to repeat the analysis. If the tissue parameter is within the preset range of the target value, the system may determine if the tissue has reached the target value, as shown in block 132. If the tissue parameter has reached the target value, the spectroscopic tissue analyzer 14 may send a signal to the tissue treatment unit 12 to stop the tissue treatment, as shown in block 134, and may annunciate the result or sound an alarm tone, or both, as previously selected by the practitioner.

If the tissue parameter is within the selected range of the target value, but has not reached the target value, the spectroscopic tissue analyzer 14 may send a signal reducing the power output, as shown in block 136, prior to repeating the analysis of the tissue parameter in block 128. This power change may be implemented to reduce the likelihood of overshooting the desired tissue parameter, resulting in unnecessary damage to the surrounding tissue. The reduction in power may be done using any number of control algorithms, such as a proportional-integral-derivative (PID) algorithm, for example. The change in the treatment power may be annunciated, if the practitioner has selected this option in block 122. Thus, once the practitioner initiates the tissue treatment, the treatment may continue automatically until the system determines that the treatment target has been reached.

B. Manual Control of Tissue Treatment

In various embodiments, the system 80 may be used for manual control of a tissue treatment, following, for example, the procedure of the block diagram shown in FIG. 5. As in the use of the system under automatic control, a manually controlled tissue treatment starts when the practitioner powers on the unit, as shown in block 138, which initializes the optics, network connections, and other circuitry. The practitioner then enters the desired control settings, as shown in block 140. Such settings may include power levels, activation time, alarm modes, and annunciation settings, and may include a setting to indicate that the system is not to send a control signal to the tissue treatment device. The practitioner places the the tissue treatment probe 16 and the optical probe 22 in contact with the tissue 84 to be analyzed, as shown in block 142. Once the probes 16 and 22 are in contact with the tissue, the system analyzes the tissue parameter, as shown in block 144. The results may be annunciated if this option was selected by the practitioner in block 140. If a target tissue parameter has been selected by the practitioner, the analysis results may be compared to the target, as shown in block 146. If the target tissue parameter is not detected, the spectroscopic tissue analyzer 14 may determine if the probe is still in contact with a tissue, as shown in block 148. If not, as shown in block 150, the system may sound an alarm tone, or annunciate this result, prior to returning to block 144 to repeat the analysis.

If the analysis in block 146 indicates that the target tissue parameter is present, the system may sound an alarm tone or annunciate this result, as shown in block 152. The practitioner may use the alarm tone or annunciation of the result to determine whether to initiate or halt the tissue treatment, as shown in block 154. The spectroscopic tissue analyzer 14 then returns to block 144 to continue the tissue analysis. Although the automatic and manual procedures have been shown as separate procedures, those skilled in the art will realize that a practitioner may change the settings to move from one to the other at any time during the tissue treatment.

VI. Combined Probes for Tissue Treatment

While the embodiments of the tissue treatment system 80 described above with respect to FIG. 3, and illustrated in FIG. 1, have shown the use of two probes for the control of tissue treatment, in other embodiments the same functionality may be obtained using probes that combine the functionality of a tissue treatment probe 16 with the functionality of an optical probe 22. For certain types of procedures, a combined probe that allows the analysis of the tissue parameter to take place at the same point as the tissue treatment may make the treatment more effective. For example, by minimizing the separation of the treatment and analysis points a combined probe may further minimize damage to adjoining tissue. Combined probes for heat sealing a vessel, removing a tissue, or freezing a tissue are discussed below.

A. A Combined Probe for Heat Sealing a Tissue

Figure 6:
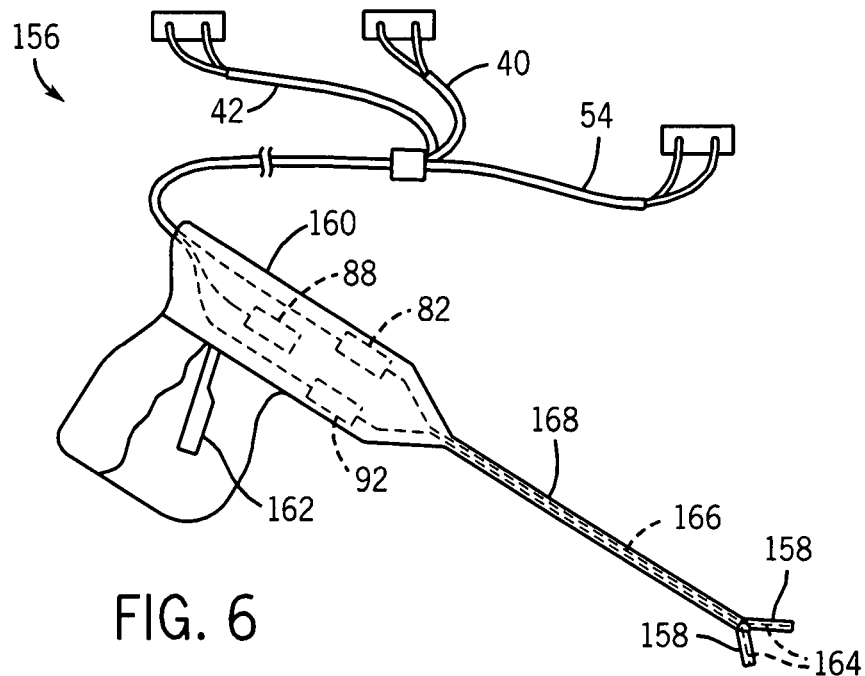
FIG. 6 is a perspective view of a laparoscopic probe that is used for the heat sealing of vessels while analyzing a tissue parameter in accordance with embodiments of the present techniques.

In an embodiment of the present techniques, a combined probe 156 may be used for heat sealing a vessel, such as by heating with RF energy. FIG. 6 is a perspective view of a probe 156 that may be used in laparoscopic procedures, during which it may be inserted into a patient's body through a small incision. The probe 156 has flat jaws 158 which may be used to clamp and heat seal vessels within the patient. The jaws 158 may be connected by a probe cable 42 to a tissue treatment device 12 comprising an RF generator. The probe has a body 160 that may contain emitters 82, detectors 92, and an encoder 88, which are connected to a spectroscopic tissue analyzer 14 through a cable 54. Further, the probe has a trigger 162, which may be connected to the tissue treatment system 80 by a cable 40. Alternatively, the emitters 82 and detectors 92 may be located within the spectroscopic tissue analyzer 14 as discussed above.

The sealing of a vessel is performed by placing the jaws 158 over the target vessel, and then clamping the jaws 158 together and activating the tissue treatment unit. Both actions may be performed by pulling the trigger 162 of the probe 160 back towards the handle. This may send a signal to the tissue treatment system 80 through the control cables 40. Those skilled in the art will recognize that other devices, such as a foot pedal, may be used to activate the tissue treatment. In an automated procedure, the activation will start a tissue treatment cycle, as discussed with reference to FIG. 4. In manual operation, the activation will start the operation of the tissue treatment device 12, as discussed with reference to FIG. 5.

The jaws 158 of the probe 160 may contain optics 164 that are coupled to the emitters 82 and detectors 92 in the handle 160 by fiber optic bundles 166 running through the body 168 of the probe. In one embodiment, the optics 164 in the jaw 158 may be configured to transmit light through the clamped vessel, with additional optics 164 in the opposing jaw 158 to receive the transmitted light and return it to the detectors 86. In another embodiment, the optics 164 in the jaws 158 may be configured to reflect light onto the vessel, prior to capturing the light and returning it to the detectors 92.

B. A Combined Probe for Removing Tissue

Figure 7:
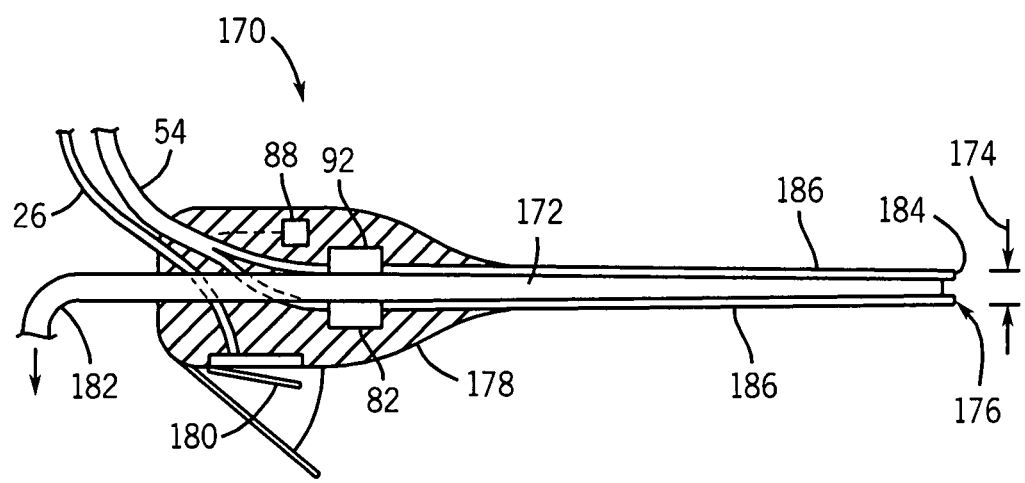
FIG. 7 is a cut away view of a suction probe in accordance with embodiments of the present invention.

In addition to heat sealing vessels, embodiments of the current techniques may be used in other types of procedures. For example, FIG. 7 is a cut away view of a suction probe 170 that may be used in embodiments of the current invention.

The suction probe 170 has a hollow body 172 to allow the removal of fluids or tissues from a cavity by a suction device.

The probe 172 may be sized appropriately for the application. For example, the diameter 174 of the tip 176 may be a large needle used for chest drainage (12 gauge) or a liposuction cannula (greater than 5 mm). The suction probe 170 has a handle 178 which may contain emitters 82, detectors 92, and encoders 88 connected to a spectroscopic tissue analyzer 14 by a spectroscopic probe cable 54. The handle may also contain a control switch 180 connected to the tissue treatment system 80 by a control cable 40. A flexible tube 182 is used to connect the hollow body 172 to the tissue treatment device 12, which is a suction unit in this embodiment. The emitters 82 and detectors 86 in the handle 178 may be connected to optics 184 at the tip 176 of the suction probe 170 by optical fibers 186.

The suction probe 170 may be used, for example, for the removal of fat cells or liquids from body cavities during surgical procedures. The use of a spectroscopic tissue analyzer 14 connected to the optics 184 at the tip 176 of the probe 170 allows for analysis of the parameter of the tissue 84 at the tip 176. Such analysis may be performed using the algorithms discussed above. This tissue analysis may help identify the type of tissue or material located at the tip 176, ensuring that the correct tissues are removed.

C. A Combined Probe for Freezing Tissue

Figure 8:
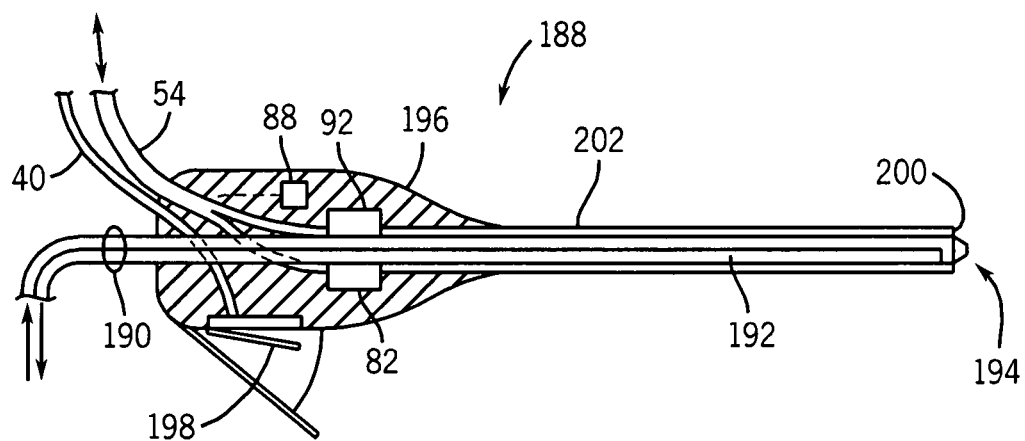
FIG. 8 is a cut away view of a cryoablation probe, or cryoprobe in accordance with embodiments of the present invention.

Another procedure that may benefit from combining the tissue analysis and treatment functions is cryoablation. FIG. 8 is a cut away view of a cryoprobe 188 that may be used in embodiments of the present techniques. This probe 188 connects to a tissue treatment device 12 comprising a cryogenic refrigeration system (not shown) through coolant tubing lines 190. Coolant tubes 192 form the core of the cryoprobe 188, carrying the coolant to the tip 194 of the cryoprobe 188. The handle 196 is insulated to protect the practitioner from the cryogenic temperatures. The handle 196 may also contain a switch 198 connected to a control cable 40 to activate the tissue treatment. Further, the handle 196 may contain emitters 82, detectors 92, and an encoder 88, which are connected to the spectroscopic tissue analyzer 14 by a cable 54. The emitters 82 and detectors 92 may be coupled to optics 200 located around the probe tip 194 by fiber optic bundles 202 running along the outside of the hollow tubes 192.

The probe 188 would be placed into contact with a tissue and the treatment activated, for example, by compressing the switch 198. Upon activation, the spectroscopic tissue analyzer 14 (see FIG. 3) would determine the percentage of the water in the tissues that is frozen. As discussed with respect to FIGS. 4 and 5, this could be used to automatically or manually control the tissue treatment sequence.

While the invention may be susceptible to various modifications and alternative forms, specific embodiments have been shown by way of example in the drawings and will be described in detail herein. However, it should be understood that the invention is not intended to be limited to the particular forms disclosed. Furthermore, those skilled in the art will recognize that the techniques discussed may be used in any number of medical settings, including for tissue treatment during invasive and non-invasive surgical procedures, and may include use of the systems for tissue treatment during visits to the office of a medical practitioner. Indeed, the invention is to cover all modifications, equivalents and alternatives falling within the spirit and scope of the invention as defined by the following appended claims.

What is claimed is:

1. A method for a medical procedure, comprising:
analyzing a parameter of a tissue using a spectroscopic tissue analyzer, wherein the parameter of the tissue comprises at least a concentration of ice of the tissue and a loss in water content of the tissue; and
controlling a tissue treatment device using a feedback signal from the spectroscopic tissue analyzer, wherein the feedback signal is based at least in part upon a comparison of the concentration of ice of the tissue and the loss in the water content of the tissue, and wherein the tissue treatment device comprises at least a tissue cryoablation unit.

2. The method of claim 1, comprising manually adjusting the tissue treatment device based on the feedback signal.

3. The method of claim 1 wherein the feedback signal automatically controls the tissue treatment device.

4. The method of claim 1 wherein the parameter of the tissue comprises at least a lipid content of the tissue, a protein arrangement in the tissue, or combinations thereof.

5. The method of claim 1 wherein the feedback signal comprises at least one of an alarm tone, a voice annunciation of the parameter of the tissue, an automatic control signal sent to the tissue treatment device, or combinations thereof.

6. A system for use in a medical procedure, comprising:
a first optical system configured to deliver electromagnetic radiation to a tissue;
a second optical system configured to receive the electromagnetic radiation from the tissue to determine at least a water content of the tissue and a concentration of ice of the tissue;
one or more active sites configured to freeze the tissue based at least in part on a feedback signal from a spectroscopic tissue analyzer, wherein the feedback signal is based at least in part upon a comparison of a loss in the water content of the tissue and the concentration of ice of the tissue, wherein the one or more active sites are disposed adjacent to the first and second optical systems.

7. The system of claim 6 wherein the first and second optical systems comprise fiber optic lines.

8. The system of claim 6 comprising a fiber optic cable for connection to the spectroscopic tissue analyzer.

9. The system of claim 6 comprising at least one of a cable or tube for connection to one or more tissue treatment devices.

10. A method, comprising:
providing a probe for delivering a tissue treatment, wherein the tissue treatment comprises at least freezing a tissue adjacent to a tip of the probe based at least in part on a comparison of a loss in water content of the tissue adjacent to the tip of the probe and a concentration of ice of the tissue adjacent to the tip of the probe; and
attaching an optical system to the probe, wherein the optical system is configured to determine the loss in the water content of the tissue adjacent to the tip of the probe and the concentration of ice of the tissue adjacent to the tip of the probe, wherein the optical system is configured to deliver electromagnetic radiation to the tissue adjacent to the tip of the probe and capture the electromagnetic radiation from the tissue adjacent to the tip of the probe.

11. The method of claim 10 wherein providing the probe for delivering the tissue treatment comprises providing at least one of a suction device configured to remove substances or a heat based tissue sealing device.

12. The method of claim 10 comprising attaching a control switch and a control cable to the probe for activation of the tissue treatment.

* * * * *